(12) United States Patent
Okumura et al.

(10) Patent No.: US 7,452,949 B2
(45) Date of Patent: Nov. 18, 2008

(54) ORGANOMETALLIC TRANSITION METAL COMPOUND, BISCYCLOPENTADIENYL LIGAND SYSTEM, CATALYST SYSTEM AND PREPARATION OF POLYOLEFINS

(75) Inventors: Yoshikuni Okumura, Kanagawa (JP); Ilya Nifant'ev, Moscow (RU); Michael J. Elder, Columbia, MD (US); Pavel V. Ivchenko, Moscow (RU); Vladimir V. Bagrov, Moscow (RU)

(73) Assignee: Basell Polyolefine GmbH, Wesseling (DE)

( * ) Notice: Subject to any disclaimer, the term of this patent is extended or adjusted under 35 U.S.C. 154(b) by 208 days.

(21) Appl. No.: 10/581,985

(22) PCT Filed: Dec. 6, 2004

(86) PCT No.: PCT/EP2004/013827

§ 371 (c)(1),
(2), (4) Date: Jun. 7, 2006

(87) PCT Pub. No.: WO2005/058916

PCT Pub. Date: Jun. 30, 2005

(65) Prior Publication Data

US 2007/0155919 A1    Jul. 5, 2007

Related U.S. Application Data

(60) Provisional application No. 60/541,668, filed on Feb. 3, 2004.

(30) Foreign Application Priority Data

Dec. 10, 2003    (DE) ................. 103 58 082

(51) Int. Cl.
*C08F 4/42* (2006.01)
(52) U.S. Cl. .............. 526/160; 526/170; 526/943; 526/348; 556/53
(58) Field of Classification Search .......... 556/53; 526/160, 70, 943, 348
See application file for complete search history.

(56) References Cited

U.S. PATENT DOCUMENTS

| | | | |
|---|---|---|---|
| 5,789,634 A | | 8/1998 | Sullivan et al. |
| 6,057,408 A | | 5/2000 | Winter et al. |
| 6,084,115 A | * | 7/2000 | Chen et al. ............. 556/22 |
| 6,127,563 A | | 10/2000 | Chen et al. |
| 6,136,993 A | | 10/2000 | Chen et al. |
| 6,156,844 A | * | 12/2000 | Hashimoto et al. ......... 525/240 |
| 6,194,501 B1 | * | 2/2001 | Okada et al. ............. 524/274 |
| 6,417,302 B1 | | 7/2002 | Bohnen |
| 6,576,726 B1 | * | 6/2003 | Rieger ................. 526/160 |
| 6,812,185 B2 | | 11/2004 | Fischer et al. |
| 7,053,160 B2 | | 5/2006 | Bingel et al. |
| 2003/0149199 A1 | | 8/2003 | Schottek et al. |
| 2004/0050724 A1 | | 3/2004 | Grul et al. |
| 2005/0010058 A1 | | 1/2005 | Elder et al. |
| 2006/0020096 A1 | | 1/2006 | Schottek et al. |

FOREIGN PATENT DOCUMENTS

| | | |
|---|---|---|
| EP | 728773 | 8/1996 |
| EP | 776913 | 6/1997 |
| EP | 834519 | 4/1998 |
| EP | 741371 | 11/2002 |
| WO | 96/00243 | 1/1996 |
| WO | 98/40331 | 9/1998 |
| WO | 98/40419 | 9/1998 |
| WO | 99/06414 | 2/1999 |
| WO | 03/045964 | 9/1999 |
| WO | 99/43717 | 9/1999 |
| WO | 99/46270 | 9/1999 |
| WO | 99/52950 | 10/1999 |
| WO | 99/52955 | 10/1999 |
| WO | 00/05277 | 2/2000 |
| WO | 00/31090 | 6/2000 |
| WO | 2004/050724 | 8/2000 |
| WO | 91/09882 | 2/2001 |
| WO | 01/48034 | 7/2001 |
| WO | 03/045551 | 6/2003 |

OTHER PUBLICATIONS

K. Bryliakov et al.,Organometallics, 24, p. 894-904 (2005).
M. Klapper et al., Macromol. Symp., 213, p. 131-145 (2004).
R. Halterman et al., Journ. Of Organometall. Chemistry, 568, p. 41-51 (1998).
M. Schloegi et al., Zeitschrift für, Naturforschung, 58b, p. 533-538 (2003).

* cited by examiner

*Primary Examiner*—Ling-Siu Choi
(74) *Attorney, Agent, or Firm*—William R. Reid; Jonathan L. Schuchardt

(57) ABSTRACT

The present invention relates to organometallic transition metal compounds of the formula (I)

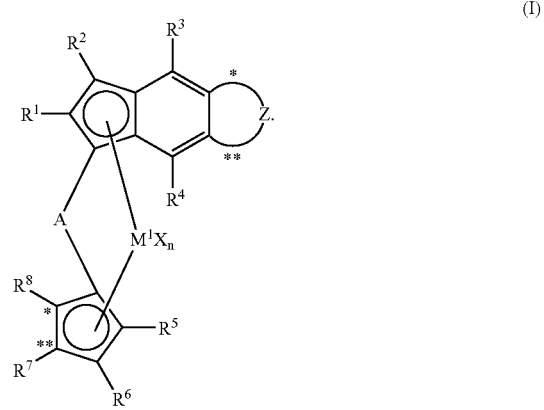

9 Claims, No Drawings

ORGANOMETALLIC TRANSITION METAL COMPOUND, BISCYCLOPENTADIENYL LIGAND SYSTEM, CATALYST SYSTEM AND PREPARATION OF POLYOLEFINS

This application is the U.S. national phase of International Application PCT/EP2004/013827, filed Dec. 6, 2004, claiming priority to German Patent Application 10358082.4 filed Dec. 10, 2003, and the benefit under 35 U.S.C. 119(e) of U.S. Provisional Application No. 60/541,668, filed Feb. 3, 2004; the disclosures of International Application PCT/EP2004/013827, German Patent Application 10358082.4 and U.S. Provisional Application No. 60/541,668, each as filed, are incorporated herein by reference.

The present invention relates to organometallic transition metal compounds of the formula (I)

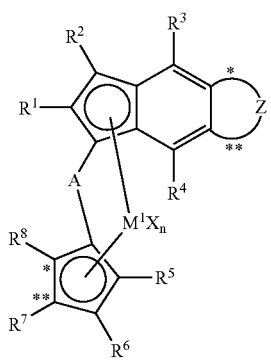

where
$M^1$ is an element of group 3, 4, 5 or 6 of the Periodic Table of the Elements or the lanthanides,
the radicals X are identical or different and are each an organic or inorganic radical, with two radicals X also being able to be joined to one another,
n is a natural number from 1 to 4,
Z is a divalent organic group which has from 1 to 40 carbon atoms and together with the two carbon atoms of the indenyl system forms a saturated or unsaturated, substituted or unsubstituted ring system having a ring size of from 4 to 12 atoms, where Z within the ring system fused to the indenyl system may also contain one or more, identical or different heteroatoms selected from the group consisting of Si, Ge, N, P, O, S, Se and Te,
$R^1$ is hydrogen or an organic radical having from 1 to 40 carbon atoms,
$R^2$ is hydrogen or an organic radical having from 1 to 40 carbon atoms,
$R^3$ is hydrogen, halogen or an organic radical having from 1 to 40 carbon atoms,
$R^4$ is hydrogen, halogen or an organic radical having from 1 to 40 carbon atoms,
$R^5$ is hydrogen or an organic radical having from 1 to 40 carbon atoms,
$R^6$ is hydrogen or an organic radical having from 1 to 40 carbon atoms,
$R^7$, $R^8$ are identical or different and are each hydrogen or an organic radical having from 1 to 40 carbon atoms or $R^7$ and $R^8$ together with the atoms connecting them form a monocyclic or polycyclic, substituted or unsubstituted ring system which has from 1 to 40 carbon atoms and may also contain heteroatoms selected from the group consisting of the elements Si, Ge, N, P, O, S, Se and Te,
A is a bridge consisting of a divalent atom or a divalent group,
and
if $R^3$ is hydrogen, then $R^5$ is an organic radical which has from 3 to 20 carbon atoms and is branched in the α position and $R^6$ is hydrogen.

The present invention further relates to biscyclopentadienyl ligand systems having such a substitution pattern, catalyst systems comprising at least one of the organometallic transition metal compounds of the present invention, a process for preparing polyolefins by polymerization or copolymerization of at least one olefin in the presence of one of the catalyst systems of the present invention, the use of the biscyclopentadienyl ligand systems of the present invention for preparing organometallic transition metal compounds and a process for preparing organometallic transition metal compounds using the biscyclopentadienyl ligand systems.

Research and development on the use of organometallic transition metal compounds, in particular metallocenes, as catalyst components for the polymerization and copolymerization of olefins with the objective of preparing tailored polyolefins has been pursued intensively in universities and in industry over the past 15 years. Now both ethylene-based polyolefins prepared by means of metallocene catalyst systems and, in particular, propylene-based polyolefins prepared by means of metallocene catalyst systems represent a dynamically growing market segment.

The preparation of propylene-ethylene copolymers which are used, for example, as rubber phase in the preparation of impact-modified propylene polymers has usually suffered from the problem that the molar masses of the propylene-ethylene copolymers which can be achieved using the known metallocene catalysts are significantly less than the molar masses of isotactic propylene homopolymers.

EP-A-776913 describes the preparation of high molecular weight propylene-ethylene copolymers using specifically substituted C2-symmetric bisindenyl metallocenes.

EP-A-834519 describes catalyst systems comprising C1-symmetric bisindenyl metallocenes which are suitable for the homopolymerization of propylene and produce propylene homopolymers having high melting points.

WO 01/48034 describes catalyst systems which, owing to specifically substituted metallocenes, are able to produce both propylene-ethylene copolymers as rubber phase having a satisfactory molar mass and also propylene homopolymers having a sufficiently high melting point for satisfactorily high stiffness of the matrix. WO 03/045551 describes catalyst systems which have a further-improved property profile in respect of the above-described requirements.

Despite the progress which has been achieved hitherto, there continues to be a need to find new metallocene catalyst systems which can achieve an improvement in the combination of high molar mass of the rubber phase and stiffness of the matrix. A further aspect is the economical accessibility of the catalyst components.

It is an object of the present invention to find organometallic transition metal compounds which, when used as catalyst constituents, are able to achieve a further increase in the molar mass of propylene-ethylene copolymers resulting from the polymerization compared to the known metallocenes and at the same time are able to increase or at least maintain the desired stiffness of the propylene homopolymer. Furthermore, the organometallic transition metal compounds should be able to be obtained in an economical fashion.

We have found that this object is achieved by the organometallic transition metal compounds of the formula (I) described at the outset.

$M^1$ is an element of group 3, 4, 5 or 6 of the Periodic Table of the Elements or the lanthanides, for example titanium, zirconium, hafnium, vanadium, niobium, tantalum, chromium, molybdenum or tungsten, preferably titanium, zirconium, hafnium, particularly preferably zirconium or hafnium and especially preferably zirconium.

The radicals X are identical or different, preferably identical, and are each an organic or inorganic radical, with two radicals X also being able to be joined to one another. X is preferably halogen, for example fluorine, chlorine, bromine, iodine, preferably chlorine, hydrogen, $C_1$-$C_{20}$—, preferably $C_1$-$C_4$-alkyl, in particular methyl, $C_2$-$C_{20}$—, preferably $C_2$-$C_4$-alkenyl, $C_6$-$C_{22}$—, preferably $C_6$-$C_{10}$-aryl, an alkylaryl or arylalkyl group having from 1 to 10, preferably from 1 to 4, carbon atoms in the alkyl radical and from 6 to 22, preferably from 6 to 10, carbon atoms in the aryl radical, —$OR^{13}$ or —$NR^{13}R^{14}$, preferably —$OR^{13}$, where two radicals X, preferably two radicals —$OR^{13}$, may also be joined to one another. It is also possible for two radicals X to form a substituted or unsubstituted diene ligand, in particular a 1,3-diene ligand. The radicals $R^{13}$ and $R^{14}$ are each $C_1$-$C_{10}$—, preferably $C_1$-$C_4$-alkyl, $C_6$-$C_{15}$—, preferably $C_6$-$C_{10}$-aryl, alkylaryl, arylalkyl, fluoroalkyl or fluoroaryl each having from 1 to 10, preferably from 1 to 4, carbon atoms in the alkyl radical and from 6 to 22, preferably from 6 to 10, carbon atoms in the aryl radical.

Unless restricted further, alkyl is a linear, branched or cyclic radical such as methyl, ethyl, n-propyl, isopropyl, n-butyl, i-butyl, s-butyl, t-butyl, n-pentyl, cyclopentyl, n-hexyl, cyclohexyl, n-heptyl or n-octyl.

The index n is a natural number from 1 to 4 which is frequently equal to the oxidation number of $M^1$ minus 2. In the case of elements of group 4 of the Periodic Table of the Elements, n is preferably 2.

Z is a divalent organic group which has from 1 to 40 carbon atoms and together with the two carbon atoms of the indenyl system forms a saturated or unsaturated, substituted or unsubstituted ring system which has a ring size of from 4 to 12, preferably from 4 to 8, particularly preferably from 4 to 6, especially preferably 5 or 6, atoms, where Z within the ring system fused to the indenyl system may also contain one or more, preferably 1 or 2, identical or different heteroatoms selected from the group consisting of Si, Ge, N, P, O, S, Se and Te, preferably Si, Ge, N, O and S, in particular O and S.

Z is preferably —$(C(R^aR^b))_k$—, —O—$(C(R^aR^b))_j$—O—, —$C(R^a)$=$C(R^a)$—$C(R^a)$=$C(R^a)$— or —$C(R^a)$=$C(R^a)$—S—, where both the radicals $R^a$ and the radicals $R^b$ are, independently of one another, identical or different and $R^a$ and $R^b$ are each hydrogen, halogen or an organic radical having from 1 to 40 carbon atoms, or two radicals $R^a$ and/or $R^b$ together with the atoms connecting them form a monocyclic or polycyclic, substituted or unsubstituted ring system which has from 1 to 30 carbon atoms and may also contain heteroatoms selected from the group consisting of the elements Si, Ge, N, P, O, S, Se and Te, in particular N, O and S, and k is a natural number from 2 to 6, preferably 3 or 4, in particular 3, and j is a natural number from 1 to 4, preferably 1 or 2, in particular 2. $R^a$ and $R^b$ are preferably each hydrogen, a $C_1$-$C_{10}$—, in particular $C_1$-$C_4$-alkyl radical or a substituted or unsubstituted $C_6$-$C_{14}$-aryl radical.

Preferred examples of Z are

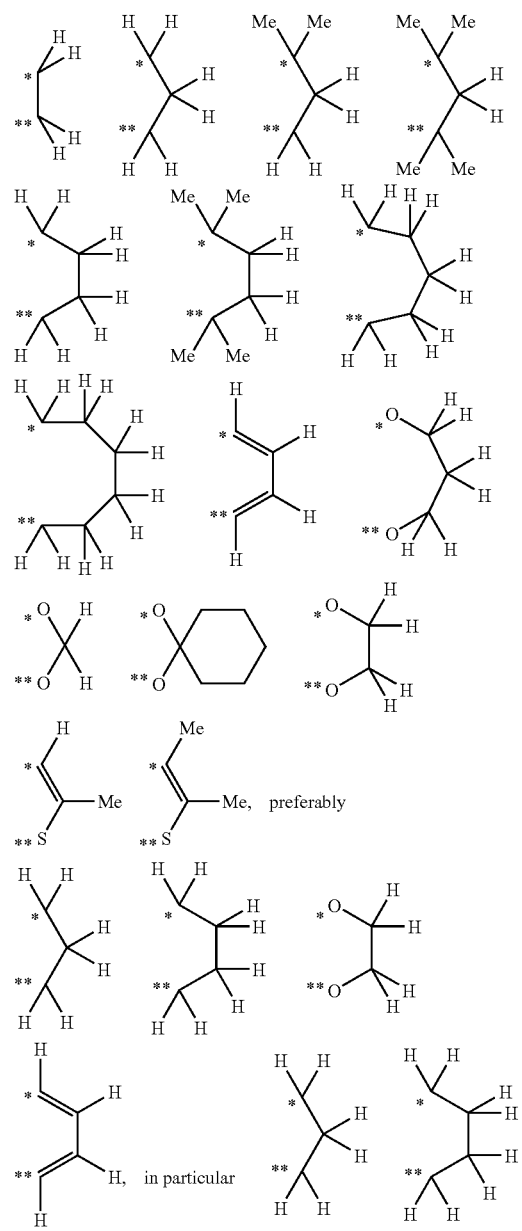

$R^1$ is hydrogen or an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl having from 1 to 10, preferably from 1 to 4, carbon atoms in the alkyl part and from 6 to 22, preferably from 6 to 10, carbon atoms in the aryl part, or a $C_2$-$C_{40}$-heteroaromatic radical containing at least one heteroatom selected from the group consisting of the elements O, N, S, P and Se, in particular O, N and S, where the heteroaromatic radical may be substituted by further radicals $R^{15}$, where $R^{15}$ is an organic radical which has from 1 to 20 carbon atoms and is defined, in particular, like $R^{13}$ and a plurality of radicals $R^{15}$ may be identical or different. $R^1$ preferably hydrogen or an organic radical which has from 1 to 40, preferably from 1 to 20, carbon atoms and is unbranched in the α position, where an organic radical which is unbranched in the α position is defined as a radical whose linking α atom is joined to not more than one atom other than hydrogen. The linking α atom of the organic radical which is unbranched in the α position is preferably a carbon atom. The radical $R^1$ is particularly preferably an unbranched $C_1$-$C_{20}$—, preferably $C_1$-$C_{10}$-n-alkyl radical, a $C_2$-$C_{20}$—, preferably $C_2$-$C_8$-alkenyl radical or an arylalkyl radical having from 1 to 10, preferably from 1 to 4, carbon atoms in the alkyl part and from 6 to 22, preferably from 6 to 10, carbon atoms in the aryl part. Examples of especially preferred radicals $R^1$ are hydrogen, methyl, ethyl, n-propyl, n-butyl, n-pentyl, n-hexyl, benzyl and 2-phenylethyl, in particular methyl, ethyl, n-propyl and n-hexyl.

$R^2$ is hydrogen or an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl each having from 1 to 10, preferably from 1 to 4, carbon atoms in the alkyl part and from 6 to 22, preferably from 6 to 10, carbon atoms in the aryl part, or a $C_2$-$C_{40}$-heteroaromatic radical containing at least one heteroatom selected from the group consisting of the elements O, N, S, P and Se, in particular O, N and S, where the heteroaromatic radical may be substituted by further radicals $R^{15}$ where $R^{15}$ is an organic radical which has from 1 to 20 carbon atoms and is defined, in particular, like $R^{13}$ and a plurality of radicals $R^{15}$ may be identical or different. $R^2$ is preferably hydrogen.

$R^3$ is hydrogen, halogen or an organic radical having from 1 to 40 carbon atoms, preferably halogen, for example fluorine, chlorine, bromine or iodine, or an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl each having from 1 to 10, preferably from 1 to 4, carbon atoms in the alkyl part and from 6 to 22, preferably from 6 to 10, carbon atoms in the aryl part, or a $C_2$-$C_{40}$-heteroaromatic radical containing at least one heteroatom selected from the group consisting of the elements O, N, S, P and Se, in particular O, N and S, where the heteroaromatic radical may be substituted by further radicals $R^{15}$, where $R^{15}$ is an organic radical which has from 1 to 20 carbon atoms and is defined, in particular, like $R^{13}$ and a plurality of radicals $R^{15}$ may be identical or different. $R^3$ is preferably a substituted or unsubstituted $C_6$-$C_{40}$-aryl radical or a $C_2$-$C_{40}$-heteroaromatic radical containing at least one heteroatom selected from the group consisting of O, N, S and P, in particular O, N and S, or the radical $R^3$ is a $C_1$-$C_{40}$—, preferably $C_3$-$C_{20}$-alkyl radical like isopropyl, cyclobutyl, 1-methylpropyl, 1-methylbutyl, 1-ethylbutyl, 1-methylpentyl, cyclopentyl, cyclohexyl or t-butyl, in particular isopropyl.

The radical $R^3$ is particularly preferably a substituted or unsubstituted $C_6$-$C_{40}$-aryl radical or alkylaryl radical having from 1 to 10, preferably from 1 to 4, carbon atoms in the alkyl part and from 6 to 22, preferably from 6 to 10, carbon atoms in the aryl part, with the radicals also being able to be halogenated. Examples of particularly preferred radicals $R^3$ are phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl) phenyl, 2,4,6-trimethylphenyl, 2,3,4-trimethylphenyl, 1-naphthyl, 2-naphthyl, phenanthrenyl, p-isopropylphenyl, p-tert-butylphenyl, p-s-butylphenyl, p-cyclohexylphenyl and p-trimethylsilylphenyl, in particular phenyl, 1-naphthyl, 3,5-dimethylphenyl and p-tert-butylphenyl.

$R^4$ is hydrogen, halogen, for example fluorine, chlorine, bromine or iodine, in particular fluorine, or an organic radical having from 1 to 10 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl each having from 1 to 10, preferably from 1 to 4, carbon atoms in the alkyl part and from 6 to 22, preferably from 6 to 10, carbon atoms in the aryl part, or a $C_2$-$C_{40}$-heteroaromatic radical containing at least one heteroatom selected from the group consisting of the elements O, N, S, P and Se, in particular O, N and S, where the heteroaromatic radical may be substituted by further radicals $R^{15}$, where $R^{15}$ is an organic radical which has from 1 to 20 carbon atoms and is, in particular, defined like $R^{13}$ and a plurality of radicals $R^{15}$ may be identical or different. $R^4$ is preferably hydrogen, fluorine, $C_1$-$C_{10}$-alkyl, in particular an n-alkyl, a substituted or unsubstituted $C_6$-$C_{40}$-aryl radical or a $C_2$-$C_{40}$-heteroaromatic radical containing at least one heteroatom selected from the group consisting of O, N, S and P, in particular O, N and S. $R^4$ is particularly preferably hydrogen, $C_1$-$C_6$-n-alkyl or a substituted or unsubstituted $C_6$-$C_{40}$-aryl radical. Examples of particularly preferred radicals $R^4$ are hydrogen, methyl, ethyl, isopropyl, n-butyl, n-hexyl, cyclohexyl, phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthrenyl, p-isopropylphenyl, p-tert-butylphenyl, p-s-butylphenyl, p-cyclohexylphenyl or p-trimethylsilylphenyl. Especial preference is given to $R^4$ being hydrogen.

$R^5$ is hydrogen or an organic radical having from 1 to 40 carbon atoms, preferably an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl each having from 1 to 10, preferably from 1 to 4, carbon atoms in the alkyl part and from 6 to 22, preferably from 6 to 10, carbon atoms in the aryl part, or a $C_2$-$C_{40}$-heteroaromatic radical containing at least one heteroatom selected from the group consisting of the elements O, N, S, P and Se, in particular O, N and S, where the heteroaromatic radical may be substituted by further radicals $R^{15}$, where $R^{15}$ is an organic radical which has from 1 to 20 carbon atoms and is, in particular, defined like $R^{13}$ and a plurality of radicals $R^{15}$ may be identical or different.

$R^5$ is preferably an organic radical which has from 3 to 20 carbon atoms and is branched in the α position, where an organic radical which is branched in the α position is defined as a radical whose linking α atom bears at least two directly bound atoms which are different from hydrogen and not more than one directly bound hydrogen atom. The linking α atom is preferably carbon. The radical $R^5$ is particularly preferably $C_3$-$C_{20}$—, preferably $C_3$-$C_{10}$-alkyl, $C_3$-$C_{20}$—, preferably $C_3$-$C_8$-alkenyl, $C_6$-$C_{18}$—, preferably $C_6$-$C_{10}$-aryl, alkylaryl, arylalkyl or arylalkenyl each having from 1 to 10, preferably from 1 to 4, carbon atoms in the alkyl part and from 6 to 18, preferably from 6 to 10, carbon atoms in the aryl part, $C_3$-$C_{12}$—, preferably $C_5$-$C_8$-cycloalkyl or cycloalkenyl, or the radical $R^5$ is a saturated or unsaturated heterocycle containing from 3 to 10 carbon atoms and at least one heteroatom selected from the group consisting of O, N, S, P and Se, preferably O, N and S, where the carbocycle or the heterocycle may be substituted by further radicals $R^{15}$, where $R^{15}$ is an organic radical which has from 1 to 10 carbon atoms and is, in particular, defined like $R^{13}$ and a plurality of radicals $R^{15}$ may be identical or different.

Examples of preferred radicals $R^5$ are isopropyl, cyclobutyl, 1-methylpropyl, 1-methylbutyl, 1-ethylbutyl, 1-methylpentyl, cyclopentyl, cyclohexyl, t-butyl, cyclopent-2-enyl, cyclopent-3-enyl, cyclohex-2-enyl, cyclohex-3-enyl, para-methylcyclohexyl, diphenylmethyl, triphenylmethyl, phenyl, 2-tolyl, 3-tolyl, 4-tolyl, 2,6-dimethylphenyl, 2,4,6-trimethylphenyl, 1-naphthyl, 2-naphthyl, phenanthryl, thienyl, furyl, methylthienyl, methylfuryl, trifluoromethyl and trimethylsilyl, with particular preference being given to isopropyl, 1-methylpropyl, 1-methylbutyl, 1-ethylbutyl, 1-methylpentyl and cyclohexyl, in particular isopropyl and cyclohexyl.

$R^6$ is hydrogen or an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl each having from 1 to 10, preferably from 1 to 4, carbon atoms in the alkyl part and from 6 to 22, preferably from 6 to 10, carbon atoms in the aryl part, or a $C_2$-$C_{40}$-heteroaromatic radical containing at least one heteroatom selected from the group consisting of the elements O, N, S, P and Se, in particular O, N and S, where the heteroaromatic radical may be substituted by further radicals $R^{15}$, where $R^{15}$ is an organic radical which has from 1 to 20 carbon atoms and is, in particular, defined like $R^{13}$ and a plurality of radicals $R^{15}$ may be identical or different. $R^6$ is preferably hydrogen.

$R^7$ and $R^8$ are identical or different and are each hydrogen or an organic radical having from 1 to 40 carbon atoms, for example a cyclic, branched or unbranched $C_1$-$C_{20}$—, preferably $C_1$-$C_8$-alkyl radical, a $C_2$-$C_{20}$—, preferably $C_2$-$C_8$-alkenyl radical, a $C_6$-$C_{22}$—, preferably $C_6$-$C_{10}$-aryl radical, an alkylaryl or arylalkyl radical having from 1 to 10, preferably from 1 to 4, carbon atoms in the alkyl part and from 6 to 22, preferably from 6 to 10, carbon atoms in the aryl part, or $R^7$ and $R^8$ together with the atoms connecting them form a monocyclic or polycyclic, substituted or unsubstituted ring system which has from 1 to 40 carbon atoms and may also contain heteroatoms selected from the group consisting of the elements Si, Ge, N, P, O, S, Se and Te, preferably Si, N, O and S, in particular S and N.

Preference is given to the radicals $R^7$ and $R^8$ together forming a divalent organic group T having from 1 to 40 carbon atoms, where T together with the two carbon atoms of the cyclopentadienyl ring forms a saturated or unsaturated, substituted or unsubstituted ring system which preferably has a ring size of from 5 to 7 atoms and T within the ring system fused to the cyclopentadienyl ring may also contain one or more, identical or different heteroatoms selected from the group consisting of Si, Ge, N, P, O, S, Se and Te, preferably Si, N, O and S, in particular S and N. Examples of preferred divalent organic groups T are

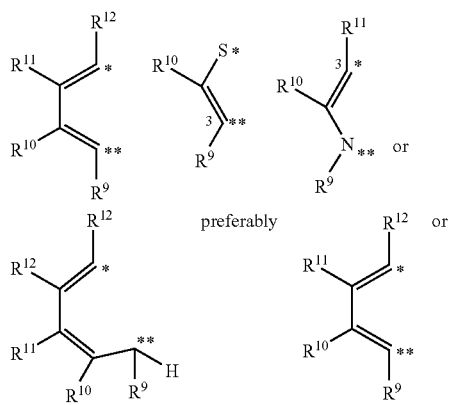

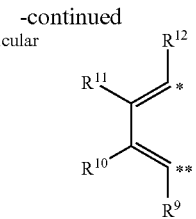

-continued where $R^9$, $R^{10}$, $R^{11}$ and $R^{12}$ are identical or different and are each hydrogen, halogen such as fluorine, chlorine, bromine or iodine, preferably fluorine, or an organic radical having from 1 to 40 carbon atoms, for example a cyclic, branched or unbranched $C_1$-$C_{20}$—, preferably $C_1$-$C_8$-alkyl radical, a $C_2$-$C_{20}$—, preferably a $C_2$-$C_8$-alkenyl radical, a $C_6$-$C_{22}$—, preferably $C_6$-$C_{10}$-aryl radical, an alkylaryl or arylalkyl radical having from 1 to 10, preferably from 1 to 4, carbon atoms in the alkyl part and from 6 to 22, preferably from 6 to 10, carbon atoms in the aryl part, where the radicals may also be halogenated, or the radicals $R^9$, $R^{10}$, $R^{11}$ and $R^{12}$ are substituted or unsubstituted, saturated or unsaturated, in particular aromatic, heterocyclic radicals which have from 2 to 40, in particular from 4 to 20, carbon atoms and contain at least one heteroatom, preferably selected from the group of elements consisting of O, N, S and P, in particular N, or two adjacent radicals $R^9$, $R^{10}$ and/or $R^{11}$ together with the atoms connecting them form a monocyclic or polycyclic, substituted or unsubstituted ring system which has from 1 to 40 carbon atoms and may also contain heteroatoms selected from the group consisting of the elements Si, Ge, N, P, O, S, Se and Te, in particular N or S.

Preference is given to $R^9$ and $R^{10}$ together forming a substituted or unsubstituted, in particular unsubstituted, 1,3-butadiene-1,4-diyl group or $R^9$ being a substituted or unsubstituted $C_6$-$C_{40}$-aryl radical or $C_2$-$C_{40}$-heteroaromatic radical containing at least one heteroatom selected from the group consisting of O, N, S and P, in particular O, N and S.

The radical $R^9$ is particularly preferably a substituted or unsubstituted $C_6$-$C_{40}$-aryl radical or an alkylaryl radical having from 1 to 10, preferably from 1 to 4, carbon atoms in the alkyl part and from 6 to 22, preferably from 6 to 10, carbon atoms in the aryl part, where the radicals may also be halogenated. Examples of particularly preferred radicals $R^9$ are phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl) phenyl, 2,4,6-trimethylphenyl, 2,3,4-trimethylphenyl, 1-naphthyl, 2-naphthyl, phenanthrenyl, p-isopropylphenyl, p-tert-butylphenyl, p-s-butylphenyl, p-cyclohexylphenyl and p-trimethylsilylphenyl, in particular phenyl, 1-naphthyl, 3,5-dimethylphenyl and p-tert-butylphenyl.

Since the steric interactions of the radicals $R^1$ and $R^5$ with the growing polymer chain are of particular importance for the polymerization behavior and the resulting properties of the polymers which can be obtained, preference is given to organometallic transition metal compounds of the formula (I) in which at least one of the radicals $R^1$ and $R^5$, in particular $R^5$, is an organic radical which is branched in the α position. Particular preference is given to organometallic transition metal compounds of the formula (I) in which the radicals $R^1$ and $R^5$ are different, in particular compounds in which $R^1$ is an organic radical which is unbranched in the α position.

A is a bridge consisting of a divalent atom or a divalent group. Examples of A are:

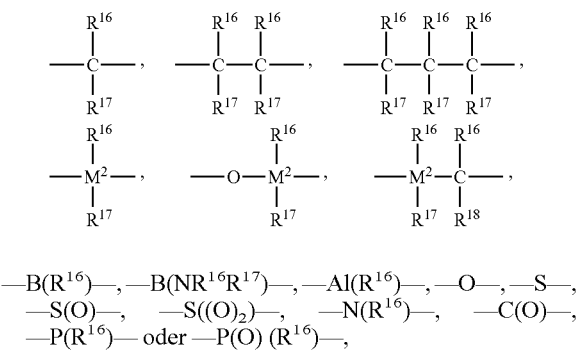

—B(R$^{16}$)—, —B(NR$^{16}$R$^{17}$)—, —Al(R$^{16}$)—, —O—, —S—, —S(O)—, —S((O)$_2$)—, —N(R$^{16}$)—, —C(O)—, —P(R$^{16}$)— oder —P(O) (R$^{16}$)—, in particular

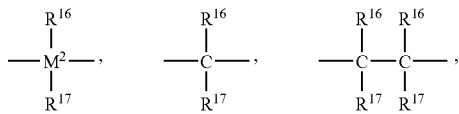

where

M$^2$ is silicon, germanium or tin, preferably silicon or germanium, particularly preferably silicon, and R$^{16}$, R$^{17}$ and R$^{18}$ are identical or different and are each a hydrogen atom, a halogen atom, a trimethylsilyl group, a C$_1$-C$_{10}$—, preferably C$_1$-C$_3$-alkyl group, a C$_1$-C$_{10}$-fluoroalkyl group, a C$_6$-C$_{10}$-fluoroaryl group, a C$_6$-C$_{10}$-aryl group, a C$_1$-C$_{10}$—, preferably C$_1$-C$_3$-alkoxy group, a C$_7$-C$_{15}$-alkylaryloxy group, a C$_2$-C$_{10}$—, preferably C$_2$-C$_4$-alkenyl group, a C$_7$-C$_{40}$-arylalkyl group, a C$_8$-C$_{40}$-arylalkenyl group or a C$_7$-C$_{40}$-alkylaryl group or two adjacent radicals together with the atoms connecting them form a saturated or unsaturated ring having from 4 to 15 carbon atoms.

Preferred embodiments of A are the bridges:

dimethylsilanediyl, methylphenylsilanediyl, diphenylsilanediyl, dimethylgermanediyl, ethylidene, 1-methylethylidene, 1,1-dimethylethylidene, 1,2-dimethylethylidene, 1,1,2,2-tetramethylethylidene, dimethylmethylidene, phenylmethylmethylidene and diphenylmethylidene, in particular dimethylsilanediyl, diphenylsilanediyl and ethylidene.

A is particularly preferably a substituted silylene group or a substituted or unsubstituted ethylene group, preferably a substituted silylene group such as dimethylsilanediyl, methylphenylsilanediyl, methyl-tert-butylsilanediyl or diphenylsilanediyl, in particular dimethylsilanediyl.

The radicals R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$ and R$^{18}$ can, according to the present invention, contain further heteroatoms, in particular heteroatoms selected from the group consisting of Si, N, P, O, S, F and Cl, or functional groups in place of carbon atoms or hydrogen atoms without the polymerization properties of the organometallic transition metal compound of the present invention being altered, as long as these heteroatoms or functional groups are chemically inert under the polymerization conditions.

Furthermore, the substituents according to the present invention are, unless restricted further, defined as follows:

The term "organic radical having from 1 to 40 carbon atoms"; as used in the present context refers to, for example, C$_1$-C$_{40}$-alkyl radicals, C$_1$-C$_{10}$-fluoroalkyl radicals, C$_1$-C$_{12}$-alkoxy radicals, saturated C$_3$-C$_{20}$-heterocyclic radicals, C$_6$-C$_{40}$-aryl radicals, C$_2$-C$_{40}$-heteroaromatic radicals, C$_6$-C$_{10}$-fluoroaryl radicals, C$_6$-C$_{10}$-aryloxy radicals, C$_3$-C$_{18}$-trialkylsilyl radicals, C$_2$-C$_{20}$-alkenyl radicals, C$_2$-C$_{20}$-alkynyl radicals, C$_7$-C$_{40}$-arylalkyl radicals or C$_8$-C$_{40}$-arylalkenyl radicals. Such an organic radical is derived from an organic compound. Thus, three different organic radicals having one carbon atom can in principle be derived from the organic compound methanol, namely methyl (H$_3$C—), methoxy (H$_3$C—O—) and hydroxymethyl(HOC(H$_2$)—).

The term "alkyl" as used in the present context encompasses linear or singly or multiply branched saturated hydrocarbons, which may also be cyclic. Preference is given to C$_1$-C$_{18}$-alkyl such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl.

The term "alkenyl" as used in the present context encompasses linear or singly or multiply branched hydrocarbons having at least one C—C double bond, if desired a plurality of C—C double bonds, which may be cumulated or alternating.

The term "saturated heterocyclic radical" as used in the present context refers, for example, to monocyclic or polycyclic, substituted or unsubstituted hydrocarbon radicals in which one or more carbon atoms, CH groups and/or CH$_2$ groups have been replaced by heteroatoms, preferably heteroatoms selected from the group consisting of O, S, N and P. Preferred examples of substituted or unsubstituted saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydrothiophenyl and the like, and also methyl-, ethyl, propyl-, isopropyl- and tert-butyl-substituted derivatives thereof.

The term "aryl" as used in the present context refers, for example, to aromatic and fused or unfused polyaromatic hydrocarbon substituents which may be monosubstituted or polysubstituted by linear or branched C$_1$-C$_{18}$-alkyl, C$_1$-C$_{18}$-alkoxy, C$_2$-C$_{10}$-alkenyl or halogen, in particular fluorine. Preferred examples of substituted and substituted aryl radicals are, in particular, phenyl, pentafluorophenyl, 4-methylphenyl, 4-ethylphenyl, 4-n-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl or 4-trifluoromethylphenyl.

The term "heteroaromatic radical" as used in the present context refers, for example, to aromatic hydrocarbon radicals in which one or more carbon atoms have been replaced by nitrogen, phosphorus, oxygen or sulfur atoms or combinations thereof. These may, like the aryl radicals, be monosubstituted or polysubstituted by linear or branched C$_1$-C$_{18}$-alkyl, C$_2$-C$_{10}$-alkenyl or halogen, in particular fluorine. Preferred examples are furyl, thienyl, pyrrolyl, pyridyl, pyrazolyl, imidazolyl, oxazolyl, thiazolyl, pyrimidinyl, pyrazinyl and the like, and also methyl-, ethyl-, propyl-, isopropyl- and tert-butyl-substituted derivatives thereof.

The term "arylalkyl" as used in the present context refers, for example, to aryl-containing substituents whose aryl radical is linked via an alkyl chain to the remainder of the molecule. Preferred examples are benzyl, substituted benzyl, phenethyl, substituted phenethyl and the like.

The terms fluoroalkyl and fluoroaryl refer to alkyl radicals and aryl radicals, respectively, in which at least one hydrogen atom, preferably more than one up to a maximum of all hydrogen atoms, of the respective substituent have been replaced by fluorine atoms. Examples of fluorine-containing substituents which are preferred according to the present invention are trifluoromethyl, 2,2,2-trifluoroethyl, pentafluorophenyl, 4-trifluoromethylphenyl, 4-perfluoro-tert-butylphenyl and the like.

Preference is given to organometallic transition metal compounds of the formula (I) in which
$R^2$ is hydrogen,
$R^5$ is an organic radical which has from 3 to 20 carbon atoms and is branched in the α position,
$R^6$ is hydrogen,
$R^1$ and $R^5$ are different and
$M^1$, X, n, Z, $R^1$, $R^3$, $R^4$, $R^7$, $R^8$ and A are as defined for the formula (I).

Special preference is given to organometallic transition metal compounds of the formula (I) according to the above definitions in which
$R^2$, $R^6$ are each hydrogen,
$R^3$ is a substituted or unsubstituted $C_6$-$C_{40}$-aryl radical or $C_2$-$C_{40}$-heteroaromatic radical containing at least one heteroatom selected from the group consisting of O, N, S and P, or $R^3$ is a $C_1$-$C_{40}$-alkyl radical,
$R^4$ is hydrogen, fluorine, $C_1$-$C_{10}$-alkyl, a substituted or unsubstituted $C_6$-$C_{40}$-aryl radical, or $C_2$-$C_{40}$-heteroaromatic radical containing at least one heteroatom selected from the group consisting of O, N, S and P,
$R^7$, $R^8$ together form a divalent organic group T having from 1 to 40 carbon atoms, where T together with the two carbon atoms of the cyclopentadienyl ring forms a saturated or unsaturated, substituted or unsubstituted ring system which has a ring size of from 5 to 7 atoms, where T within the ring system fused to the cyclopentadienyl ring may also contain one or more, identical or different heteroatoms selected from the group consisting of Si, Ge, N, P, O, S, Se and Te, and
$M^1$, X, n, $R^1$, $R^5$, Z and A are as defined for the formula (I).

Particular preference is given to organometallic transition metal compounds of the formula (I) according to the above definitions in which
$M^1$ is Ti, Zr or Hf,
n is 2,
$R^1$ is hydrogen or an organic radical which has from 1 to 20 carbon atoms and is unbranched in the α position, in particular an organic radical which has from 1 to 20 carbon atoms and is unbranched in the α position,
$R^3$ is a substituted or unsubstituted $C_6$-$C_{40}$-aryl radical and
$R^5$ is an organic radical which has from 3 to 20 carbon atoms and is branched in the α position.

Very particular preference is given to organometallic transition metal compounds of the formula (I) according to the above definitions in which
$R^7$, $R^8$ together form

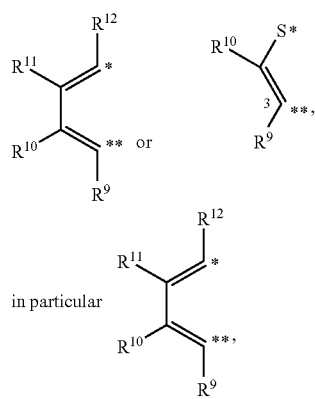

in particular where
$R^9$, $R^{10}$, $R^{11}$ and $R^{12}$ are identical or different and are each hydrogen, halogen or an organic radical having from 1 to 40 carbon atoms or two adjacent radicals $R^9$, $R^{10}$ and/or $R^{11}$ together with the atoms connecting them form a monocyclic or polycyclic, substituted or unsubstituted ring system which has from 1 to 40 carbon atoms and may also contain heteroatoms selected from the group consisting of the elements Si, Ge, N, P, O, S, Se and Te, and
A is a substituted silylene group or a substituted or unsubstituted ethylene group, in particular a substituted silylene group.

Illustrative examples of novel organometallic transition metal compounds of the formula (I), which do not, however, restrict the scope of the invention, are:
Me₂Si(6-Me-4-Ph-1,2,3,5-tetrahydro-s-indacen-7-yl)(2-i-Pr-4-Ph-inden-1-yl)ZrCl₂,
Me₂Si(6,8-Me₂-4-Ph-1,2,3,5-tetrahydro-s-indacen-7-yl)(2-i-Pr-4-Ph-inden-1-yl)ZrCl₂,
Me₂Si(6-Me-4,8-Ph₂-1,2,3,5-tetrahydro-s-indacen-7-yl)(2-i-Pr-4-Ph-inden-1-yl)ZrCl₂,
Me₂Si(6-Me-4-(4-biphenyl)-1,2,3,5-tetrahydro-s-indacen-7-yl)(2-i-Pr-4-Ph-inden-1-yl)ZrCl₂,
Me₂Si(1,1,3,3,6-Me₅-4-Ph-1,2,3,5-tetrahydro-s-indacen-7-yl)(2-i-Pr-4-Ph-inden-1-yl)ZrCl₂,
Me₂Si(2,2,6-Me₃-4-Ph-1,2,3,5-tetrahydro-s-indacen-7-yl)(2-i-Pr-4-Ph-inden-1-yl)ZrCl₂,
Me₂Si(3,3,6-Me₃-4-Ph-1,2,3,5-tetrahydro-s-indacen-7-yl)(2-i-Pr-4-Ph-inden-1-yl)ZrCl₂,
Me₂Si(2-Me-4-Ph-1H-cyclopenta[b]naphthalen-1-yl)(2-i-Pr-4-Ph-inden-1-yl)ZrCl₂,
Me₂Si(2,5,8-Me₃-4-Ph-1H-cyclopenta[b]naphthalen-1-yl)(2-i-Pr-4-Ph-inden-1-yl)ZrCl₂,
Me₂Si(2-Me-4-Ph-5,6,7,8-tetrahydro-1H-cyclopenta[b]naphthalen-1-yl)(2-i-Pr-4-Ph-inden-1-yl)ZrCl₂,
Me₂Si(2-Me-4-Ph-6,7-dihydro-1H-5,8-dioxacyclopenta[b]naphthalen-1-yl)(2-i-Pr-4-Ph-inden-1-yl)ZrCl₂,
Me₂Si(2,6-Me₂-4-Ph-5H-1-thia-s-indacen-7-yl)(2-i-Pr-4-Ph-inden-1-yl)ZrCl₂,
Me₂Si(2,3,6-Me₃-4-Ph-5H-1-thia-s-indacen-7-yl)(2-i-Pr-4-Ph-inden-1-yl)ZrCl₂,
Me₂Si(5-Me-3-Ph-2,4-dihydro-1H-cyclobuta[f]inden-6-yl)(2-i-Pr-4-Ph-inden-1-yl)ZrCl₂,
Me₂Si(2-Me-4-Ph-1,5,6,7,8,9-hexahydrocyclohepta[f]inden-1-yl)(2-i-Pr-4-Ph-inden-1-yl)ZrCl₂, tk
Me₂Si(6-(2-(5-methylfuryl))-4-Ph-1,2,3,5-tetrahydro-s-indacen-7-yl)(2-i-Pr-4-Ph-inden-1-yl)ZrCl₂,
Me₂Si(6-Me-4-Ph-1,2,3,5-tetrahydro-s-indacen-7-yl)(2-i-Pr-4-(4-t-BuPh)-inden-1-yl)ZrCl₂,
Me₂Si(6,8-Me₂-4-Ph-1,2,3,5-tetrahydro-s-indacen-7-yl)(2-i-Pr-4-(4-t-BuPh)-inden-1-yl)ZrCl₂,
Me₂Si(6-Me-4,8-Ph₂-1,2,3,5-tetrahydro-s-indacen-7-yl)(2-i-Pr-4-(4-t-BuPh)-inden-1-yl)ZrCl₂,
Me₂Si(6-Me-4-(4-biphenyl)-1,2,3,5-tetrahydro-s-indacen-7-yl)(2-i-Pr-4-(4-t-BuPh)inden-1-yl)ZrCl₂,
Me₂Si(1,1,3,3,6-Me₅-4-Ph-1,2,3,5-tetrahydro-s-indacen-7-yl)(2-i-Pr-4-(4-t-BuPh)-inden-1-yl)ZrCl₂,
Me₂Si(2,2,6-Me₃-4-Ph-1,2,3,5-tetrahydro-s-indacen-7-yl)(2-i-Pr-4-(4-t-BuPh)-inden-1-yl)ZrCl₂,
Me₂Si(3,3,6-Me₃-4-Ph-1,2,3,5-tetrahydro-s-indacen-7-yl)(2-i-Pr-4-(4-t-BuPh)-inden-1-yl)ZrCl₂,
Me₂Si(2-Me-4-Ph-1H-cyclopenta[b]naphthalen-1-yl)(2-i-Pr-4-(4-t-BuPh)-inden-1-yl)ZrCl₂,
Me₂Si(2,5,8-Me₃-4-Ph-1H-cyclopenta[b]naphthalen-1-yl)(2-i-Pr-4-(4-t-Bu Ph)-inden-1-yl)ZrCl₂,
Me₂Si(2-Me-4-Ph-5,6,7,8-tetrahydro-1H-cyclopenta[b]naphthalen-1-yl)(2-i-Pr-4-(4-t-Bu Ph)-inden-1-yl)ZrCl₂, Me$_2$Si(2-Me-4-Ph-6,7-dihydro-1H-5,8-dioxacyclopenta[b]
naphthalen-1-yl)(2-i-Pr-4-(4-t-BuPh)-inden-1-yl)ZrCl$_2$,
Me$_2$Si(2,6-Me$_2$-4-Ph-5H-1-thia-s-indacen-7-yl)(2-i-Pr-4-
(4-t-BuPh)-inden-1-yl)ZrCl$_2$,
Me$_2$Si(2,3,6-Me$_3$-4-Ph-5H-1-thia-s-indacen-7-yl)(2-i-Pr-4-
(4-t-BuPh)-inden-1-yl)ZrCl$_2$,
Me$_2$Si(5-Me-3-Ph-2,4-dihydro-1H-cyclobuta[f]inden-6-yl)
(2-i-Pr-4-(4-t-BuPh)-inden-1-yl)ZrCl$_2$,
Me$_2$Si(2-Me-4-Ph-1,5,6,7,8,9-hexahydrocyclohepta[f]inden-1-yl)(2-i-Pr-4-(4-t-BuPh)-inden-1-yl)ZrCl$_2$,
Me$_2$Si(6-Me-4-i-Pr-1,2,3,5-tetrahydro-s-indacen-7-yl)(2-i-Pr-4-(4-t-BuPh)-inden-1-yl)ZrCl$_2$,
Me$_2$Si(6-Me-4-(4-t-BuPh)-1,2,3,5-tetrahydro-s-indacen-7-yl)(2-i-Pr-4-(4-t-BuPh)-inden-1-yl)ZrCl$_2$,
Me$_2$Si(6,8-Me$_2$-4-(4-t-BuPh)-1,2,3,5-tetrahydro-s-indacen-7-yl)(2-i-Pr-4-(4-t-BuPh)-inden- 1-yl)ZrCl$_2$,
Me$_2$Si(1,1,3,3,6-Me$_5$-4-(4-t-BuPh)-1,2,3,5-tetrahydro-s-indacen-7-yl)(2-i-Pr-4-(4-t-BuPh)-inden-1-yl)ZrCl$_2$,
Me$_2$Si(2,2,6-Me$_3$-4-(4-t-BuPh)-1,2,3,5-tetrahydro-s-indacen-7-yl)(2-i-Pr-4-(4-t-BuPh)-inden-1-yl)ZrCl$_2$,
Me$_2$Si(3,3,6-Me$_3$-4-(4-t-BuPh)-1,2,3,5-tetrahydro-s-indacen-7-yl)(2-i-Pr-4-(4-t-BuPh)-inden-1-yl)ZrCl$_2$,
Me$_2$Si(2-Me-4-(4-t-BuPh)-1H-cyclopenta[b]naphthalen-1-yl)(2-i-Pr-4-(4-t-BuPh)-inden-1-yl)ZrCl$_2$,
Me$_2$Si(2,5,8-Me$_3$-4-(4-t-Bu Ph)-1H-cyclopenta[b]naphthalen-1-yl)(2-i-Pr-4-(4-t-BuPh)-inden-1-yl)ZrCl$_2$,
Me$_2$Si(2-Me-4-(4-t-Bu Ph)-5,6,7,8-tetrahydro-1H-cyclopenta[b]naphthalen-1-yl)(2-i-Pr-4-(4-t-BuPh)-inden-1-yl)ZrCl$_2$,
Me$_2$Si(2-Me-4-(4-t-Bu Ph)-6,7-dihydro-1H-5,8-dioxacyclopenta[b]naphthalen-1-yl)(2-i-Pr-4-(4-t-BuPh)-inden-1-yl)ZrCl$_2$,
Me$_2$Si(2,6-Me$_2$-4-(4-t-BuPh)-5H-1-thia-s-indacen-7-yl)(2-i-Pr-4-(4-t-BuPh)-inden-1-yl)ZrCl$_2$,
Me$_2$Si(2,3,6-Me$_3$-4-(4-t-Bu Ph)-5H-1-thia-s-indacen-7-yl)(2-i-Pr-4-(4-t-BuPh)-inden-1-yl)ZrCl$_2$,
Me$_2$Si(5-Me-3-(4-t-BuPh)-2,4-dihydro-1H-cyclobuta[f]inden-6-yl)(2-i-Pr-4-(4-t-BuPh)-inden-1-yl)ZrCl$_2$,
Me$_2$Si(2-Me-4-(4-t-BuPh)-1,5,6,7,8,9-hexahydrocyclohepta[f]inden-1-yl)(2-i-Pr-4-(4-t-BuPh)-inden-1-yl)ZrCl$_2$,
Me$_2$Si(6-Me-4-(2-MePh)-1,2,3,5-tetrahydro-s-indacen-7-yl)(2-i-Pr-4-(4-t-BuPh)-inden-1-yl)ZrCl$_2$,
Me$_2$Si(6,8-Me$_2$-4-(2-MePh)-1,2,3,5-tetrahydro-s-indacen-7-yl)(2-i-Pr-4-(4-t-Bu Ph)-inden-1-yl)ZrCl$_2$,
Me$_2$Si(1,1,3,3,6-Me$_5$-4-(2-MePh)-1,2,3,5-tetrahydro-s-indacen-7-yl)(2-i-Pr-4-(4-t-BuPh)inden-1-yl)ZrCl$_2$,
Me$_2$Si(2,2,6-Me$_3$-4-(2-MePh)-1,2,3,5-tetrahydro-s-indacen-7-yl)(2-i-Pr-4-(4-t-Bu Ph)-inden-1-yl)ZrCl$_2$,
Me$_2$Si(3,3,6-Me$_3$-4-(2-MePh)-1,2,3,5-tetrahydro-s-indacen-7-yl)(2-i-Pr-4-(4-t-BuPh)-inden-1-yl)ZrCl$_2$,
Me$_2$Si(2-Me-4-(2-MePh)-1H-cyclopenta[b]naphthalen-1-yl)(2-i-Pr-4-(4-t-BuPh)-inden-1-yl)ZrCl$_2$,
Me$_2$Si(2,5,8-Me$_3$-4-(2-MePh)-1H-cyclopenta[b]naphthalen-1-yl)(2-i-Pr-4-(4-t-BuPh)-inden-1-yl)ZrCl$_2$,
Me$_2$Si(2-Me-4-(2-MePh)-5,6,7,8-tetrahydro-1H-cyclopenta[b]naphthalen-1-yl)(2-i-Pr-4-(4-t-BuPh)-inden-1-yl)ZrCl$_2$,
Me$_2$Si(2-Me-4-(2-MePh)-6,7-dihydro-1H-5,8-dioxacyclopenta[b]naphthalen-1-yl)(2-i-Pr-4-(4-t-BuPh)-inden-1-yl)ZrCl$_2$,
Me$_2$Si(2,6-Me$_2$4-(2-MePh)-5H-1-thia-s-indacen-7-yl)(2-i-Pr-4-(4-t-BuPh)-inden-1-yl)ZrCl$_2$,
Me$_2$Si(2,3,6-Me$_3$-4-(2-MePh)-5H-1-thia-s-indacen-7-yl)(2-i-Pr-4-(4-t-BuPh)-inden-1-yl)ZrCl$_2$,
Me$_2$Si(5-Me-3-(2-MePh)-2,4-dihydro-1H-cyclobuta[f]inden-6-yl)(2-i-Pr-4-(4-t-BuPh)-inden-1-yl)ZrCl$_2$,
Me$_2$Si(2-Me-4-(2-MePh)-1,5,6,7,8,9-hexahydrocyclohepta[f]inden-1-yl)(2-i-Pr-4-(4-t-BuPh)-inden-1-yl)ZrCl$_2$,
Me$_2$Si(6-Me-4-(2,5-Me$_2$Ph)-1,2,3,5-tetrahydro-s-indacen-7-yl)(2-i-Pr-4-(4-t-BuPh)-inden-1-yl)ZrCl$_2$,
Me$_2$Si(6,8-Me$_2$-4-(2,5-Me$_2$Ph)-1,2,3,5-tetrahydro-s-indacen-7-yl)(2-i-Pr-4-(4-t-Bu Ph)-inden-1-yl)ZrCl$_2$,
Me$_2$Si(1,1,3,3,6-Me$_5$-4-(2,5-Me$_2$Ph)-1,2,3,5-tetrahydro-s-indacen-7-yl)(2-i-Pr-4-(4-t-BuPh)-inden-1-yl)ZrCl$_2$,
Me$_2$Si(2,2,6-Me$_3$-4-(2,5-Me$_2$Ph)-1,2,3,5-tetrahydro-s-indacen-7-yl)(2-i-Pr-4-(4-t-Bu Ph)-inden-1-yl)ZrCl$_2$,
Me$_2$Si(3,3,6-Me$_3$-4-(2,5-M e$_2$Ph)-1,2,3,5-tetrahydro-s-indacen-7-yl)(2-i-Pr-4-(4-t-Bu Ph)-inden-1-yl)ZrCl$_2$,
Me$_2$Si(2-Me-4-(2,5-Me$_2$Ph)-1H-cyclopenta[b]naphthalen-1-yl)(2-i-Pr-4-(4-t-BuPh)-inden-1-yl)ZrCl$_2$,
Me$_2$Si(2,5,8-Me$_3$-4-(2,5-M e$_2$Ph)-1H-cyclopenta[b]naphthalen-1-yl)(2-i-Pr-4-(4-t-Bu Ph)-inden-1-yl)ZrCl$_2$,
Me$_2$Si(2-Me-4-(2,5-Me$_2$Ph)-5,6,7,8-tetrahydro-1H-cyclopenta[b]naphthalen-1-yl)(2-i-Pr-4-(4-t-BuPh)-inden-1-yl)ZrCl$_2$,
Me$_2$Si(2-Me-4-(2,5-Me$_2$Ph)-6,7-dihydro-1H-5,8-dioxacyclopenta[b]naphthalen-1-yl)(2-i-Pr-4-(4-t-BuPh)-inden-1-yl)ZrCl$_2$,
Me$_2$Si(2,6-Me$_2$-4-(2,5-Me$_2$Ph)-5H-1-thia-s-indacen-7-yl)(2-i-Pr-4-(4-t-BuPh)-inden-1-yl)ZrCl$_2$,
Me$_2$Si(2,3,6-Me$_3$-4-(2,5-Me$_2$Ph)-5H-1-thia-s-indacen-7-yl)(2-i-Pr-4-(4-t-Bu Ph)-inden-1-yl)ZrCl$_2$,
Me$_2$Si(5-Me-3-(2,5-Me$_2$Ph)-2,4-dihydro-1H-cyclobuta[f]inden-6-yl)(2-i-Pr-4-(4-t-Bu Ph)inden-1-yl)ZrCl$_2$,
Me$_2$Si(2-Me-4-(2,5-Me$_2$Ph)-1,5,6,7,8,9-hexahydrocyclohepta[f]inden-1-yl)(2-i-Pr-4-(4-t-BuPh)-inden-1-yl)ZrCl$_2$,
Me$_2$Si(6-Me-4-Ph-1,2,3,5-tetrahydro-s-indacen-7-yl)(5-i-Pr-3-Ph-2-Me-cyclopenta[2,3-b]thiophen-6-yl)ZrCl$_2$,
Me$_2$Si(6-Me-4-(2,5-Me$_2$Ph)-1,2,3,5-tetrahydro-s-indacen-7-yl)(5-i-Pr-3-Ph-2-Me-cyclopenta-[2,3-b]thiophen-6-yl)ZrCl$_2$,
Me$_2$Si(6,8-Me$_2$-4-Ph-1,2,3,5-tetrahydro-s-indacen-7-yl)(5-i-Pr-3-Ph-2-Me-cyclopenta-[2,3-b]thiophen-6-yl)ZrCl$_2$,
Me$_2$Si(1,1,3,3,6-Me$_5$-4-Ph-1,2,3,5-tetrahydro-s-indacen-7-yl)(5-i-Pr-3-Ph-2-Me-cyclopenta-[2,3-b]thiophen-6-yl)ZrCl$_2$,
Me$_2$Si(2,2,6-Me$_3$-4-Ph-1,2,3,5-tetrahydro-s-indacen-7-yl)(5-i-Pr-3-Ph-2-Me-cyclopenta-[2,3-b]thiophen-6-yl)ZrCl$_2$,
Me$_2$Si(3,3,6-Me$_3$-4-Ph-1,2,3,5-tetrahydro-s-indacen-7-yl)(5-i-Pr-3-Ph-2-Me-cyclopenta-[2,3-b]thiophen-6-yl)ZrCl$_2$,
Me$_2$Si(2-Me-4-Ph-1H-cyclopenta[b]naphthalen-1-yl)(5-i-Pr-3-Ph-2-Me-cyclopenta[2,3-b]thiophen-6-yl)ZrCl$_2$,
Me$_2$Si(2,5,8-Me$_3$-4-Ph-1H-cyclopenta[b]naphthalen-1-yl)(5-i-Pr-3-Ph-2-Me-cyclopenta-[2,3-b]thiophen-6-yl)ZrCl$_2$,
Me$_2$Si(2-Me-4-Ph-5,6,7,8-tetrahydro-1H-cyclopenta[b]naphthalen-1-yl)(5-i-Pr-3-Ph-2-Me-cyclopenta[2,3-b]thiophen-6-yl)ZrCl$_2$,
Me$_2$Si(2-Me-4-Ph-6,7-dihydro-1H-5,8-dioxacyclopenta[b]naphthalen-1-yl)(5-i-Pr-3-Ph-2-Me-cyclopenta[2,3-b]thiophen-6-yl)ZrCl$_2$,
Me$_2$Si(2,6-Me$_2$-4-Ph-5H-1-thia-s-indacen-7-yl)(5-i-Pr-3-Ph-2-Me-cyclopenta[2,3-b]thiophen-6-yl)ZrCl$_2$,
Me$_2$Si(2,3,6-Me$_3$-4-Ph-5H-1-thia-s-indacen-7-yl)(5-i-Pr-3-Ph-2-Me-cyclopenta[2,3-b]thiophen-6-yl)ZrCl$_2$,
Me$_2$Si(5-Me-3-Ph-2,4-dihydro-1H-cyclobuta[f]inden-6-yl)(5-i-Pr-3-Ph-2-Me-cyclopenta-[2,3-b]thiophen-6-yl)ZrCl$_2$, Me$_2$Si(2-Me-4-Ph-1,5,6,7,8,9-hexahydrocyclohepta[f]inden-1-yl)(5-i-Pr-3-Ph-2-Me-cyclopenta-[2,3-b]thiophen-6-yl)ZrCl$_2$,
Me$_2$Si(6-Me-4-Ph-1,2,3,5-tetrahydro-s-indacen-7-yl)(5-i-Pr-1-Ph-2-Me-cyclopenta[2,3-b]pyrrol-4-yl)ZrCl$_2$,
Me$_2$Si(6,8-Me$_2$-4-Ph-1,2,3,5-tetrahydro-s-indacen-7-yl)(5-i-Pr-1-Ph-2-Me-cyclopenta[2,3-b]pyrrol-4-yl)ZrCl$_2$,
Me$_2$Si(1,1,3,3,6-Me$_5$-4-Ph-1,2,3,5-tetrahydro-s-indacen-7-yl)(5-i-Pr-1-Ph-2-Me-cyclopenta-[2,3-b]pyrrol-4-yl)ZrCl$_2$,
Me$_2$Si(2,2,6-Me$_3$-4-Ph-1,2,3,5-tetrahydro-s-indacen-7-yl)(5-i-Pr-1-Ph-2-Me-cyclopenta-[2,3-b]pyrrol-4-yl)ZrCl$_2$,
Me$_2$Si(3,3,6-Me$_3$-4-Ph-1,2,3,5-tetrahydro-s-indacen-7-yl)(5-i-Pr-1-Ph-2-Me-cyclopenta-[2,3-b]pyrrol-4-yl)ZrCl$_2$,
Me$_2$Si(2-Me-4-Ph-1H-cyclopenta[b]naphthalen-1-yl)(5-i-Pr-1-Ph-2-Me-cyclopenta[2,3-b]pyrrol-4-yl)ZrCl$_2$,
Me$_2$Si(2,5,8-Me$_3$-4-Ph-1H-cyclopenta[b]naphthalen-1-yl)(5-i-Pr-1-Ph-2-Me-cyclopenta-[2,3-b]pyrrol-4-yl)ZrCl$_2$,
Me$_2$Si(2-Me-4-Ph-5,6,7,8-tetrahydro-1H-cyclopenta[b]naphthalen-1-yl)(5-i-Pr-1-Ph-2-Me-cyclopenta[2,3-b]pyrrol-4-yl)ZrCl$_2$,
Me$_2$Si(2-Me-4-Ph-6,7-dihydro-1H-5,8-dioxacyclopenta[b]naphthalen-1-yl)(5-i-Pr-1-Ph-2-Me-cyclopenta[2,3-b]pyrrol-4-yl)ZrCl$_2$,
Me$_2$Si(2,6-Me$_2$-4-Ph-5H-1-thia-s-indacen-7-yl)(5-i-Pr-1-Ph-2-Me-cyclopenta[2,3-b]pyrrol-4-yl)ZrCl$_2$,
Me$_2$Si(2,3,6-Me$_3$-4-Ph-5H-1-thia-s-indacen-7-yl)(5-i-Pr-1-Ph-2-Me-cyclopenta[2,3-b]pyrrol-4-yl)ZrCl$_2$,
Me$_2$Si(5-Me-3-Ph-2,4-dihydro-1H-cyclobuta[f]inden-6-yl)(5-i-Pr-1-Ph-2-Me-cyclopenta-[2,3-b]pyrrol-4-yl)ZrCl$_2$,
Me$_2$Si(2-Me-4-Ph-1,5,6,7,8,9-hexahydrocyclohepta[f]inden-1-yl)(5-i-Pr-1-Ph-2-Me-cyclopenta-[2,3-b]pyrrol-4-yl)ZrCl$_2$ The nomenclature and the numbering of the ring atoms corresponds to the following examples:

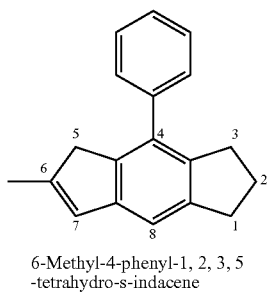

6-Methyl-4-phenyl-1, 2, 3, 5-tetrahydro-s-indacene

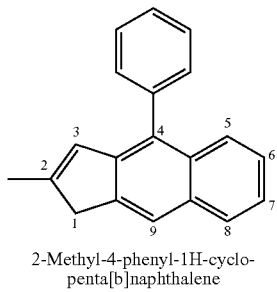

2-Methyl-4-phenyl-1H-cyclopenta[b]naphthalene

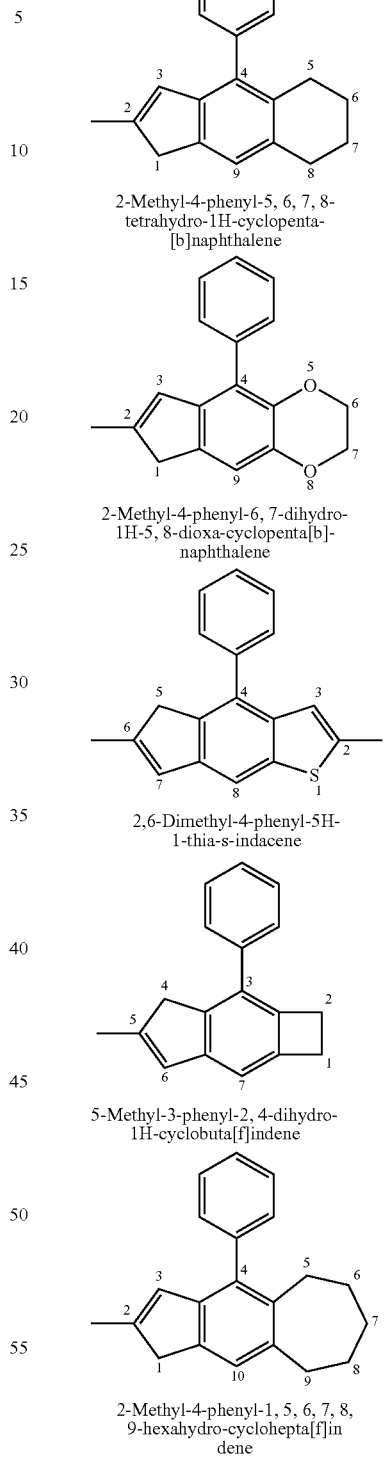

2-Methyl-4-phenyl-5, 6, 7, 8-tetrahydro-1H-cyclopenta-[b]naphthalene

2-Methyl-4-phenyl-6, 7-dihydro-1H-5, 8-dioxa-cyclopenta[b]-naphthalene 2,6-Dimethyl-4-phenyl-5H-1-thia-s-indacene 5-Methyl-3-phenyl-2, 4-dihydro-1H-cyclobuta[f]indene 2-Methyl-4-phenyl-1, 5, 6, 7, 8, 9-hexahydro-cyclohepta[f]indene Compared to the previously known metallocenes, the novel organometallic transition metal compounds of the formula (I) give an increase in the previously achievable molar masses in the copolymerization of propylene with ethylene, and at the same time give a satisfactory molar mass and a high meting point of the isotactic polypropylene in the homopolymerization of propylene.

The novel metallocenes of the formula (I) can be prepared by methods as described in WO 01/48034. These methods usually produce the organometallic transition metal compounds of the formula (I) together with a further diastereomer.

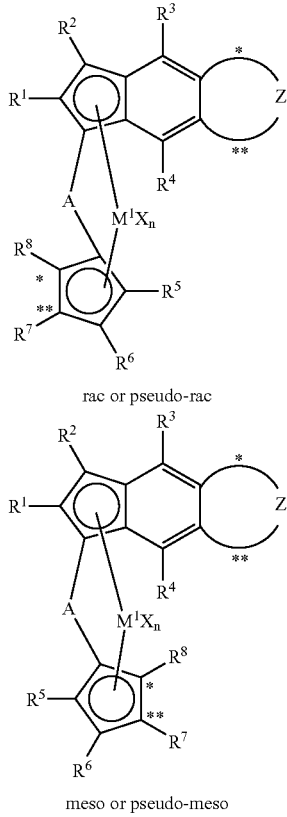

rac or pseudo-rac meso or pseudo-meso

The organometallic transition metal compounds of the formula (I) (rac or pseudo-rac) can also be used as a diastereomer mixture with the undesired diastereomers coproduced in their synthesis (meso or pseudo-meso) in the preparation of the catalyst. The organometallic transition metal compounds of the formula (I) produce highly isotactic polypropylene, while the corresponding undesired diastereomers generally give atactic polypropylene.

The separation of the diastereomers is known in principle.

The invention further provides biscyclopentadienyl ligand systems of the formula (II)

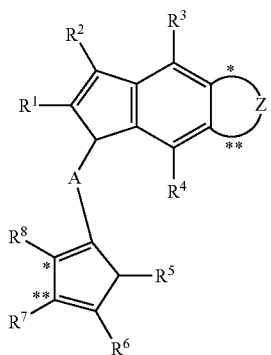

or its double bond isomers, where the variables $R^1, R^2, R^3, R^4, R^5, R^6, R^7, R^8, Z$ and $A$ are as defined for the formula (I).

The substitution pattern of the biscyclopentadienyl ligand systems of the formula (II) is critical for the particular polymerization properties of the organometallic transition metal compounds containing these biscyclopentadienyl ligand systems.

The invention further provides for the use of a biscyclopentadienyl ligand system of the formula (II) for preparing an organometallic transition metal compound, preferably for preparing an organometallic transition metal compound of an element of group 4 of the Periodic Table of the Elements, in particular zirconium.

Thus, a process for preparing an organometallic transition metal compound which comprises reacting a biscyclopentadienyl ligand system of the formula (II) or a bisanion prepared therefrom with a transition metal compound is also subject matter of the present invention. It is usual firstly to doubly deprotonate a ligand system of the formula (II) using a base such as n-butyllithium and subsequently to react the resulting bisanion with a suitable transition metal source such as zirconium tetrachloride. As an alternative, the uncharged biscyclopentadienyl ligand system of the formula (II) can be reacted directly with a suitable transition metal source which has strongly basic ligands, for example tetrakis(dimethylamino)zirconium.

The steric interaction of the radical $R^5$ of the one cyclopentadienyl ligand with the divalent group Z of the second cyclopentadienyl ligand is of particular importance for the polymerization properties of the organometallic transition metal compound of the formula (I)

Indenes of the formula (IIIa) or their double bond isomers of the formula (IIIb)

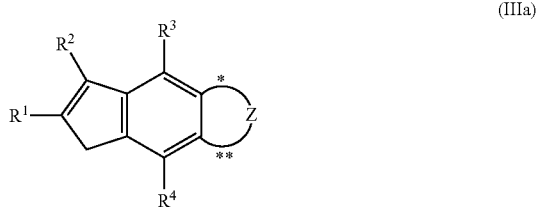

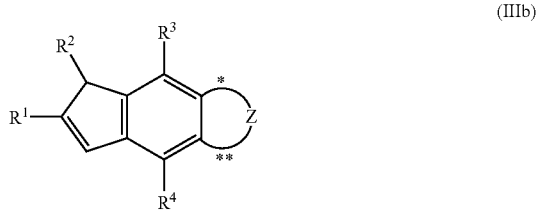

where the variables $R^1, R^2, R^3, R^4$ and Z are as defined for the formula (I)

can be prepared from known or readily obtainable precursors. Preference is given to a process in which an indanone of the formula (IV) is converted into an indanone of the formula (V) bearing a leaving group L, where L is preferably a halogen, in particular bromine. The leaving group L is subsequently, as described, for example, in WO 98/40331, replaced by the radical $R^3$ and the resulting indanone (VI) is reduced to form the indanol which is subsequently dehydrated to give the indene of the formula (IIIa) or (IIIb).

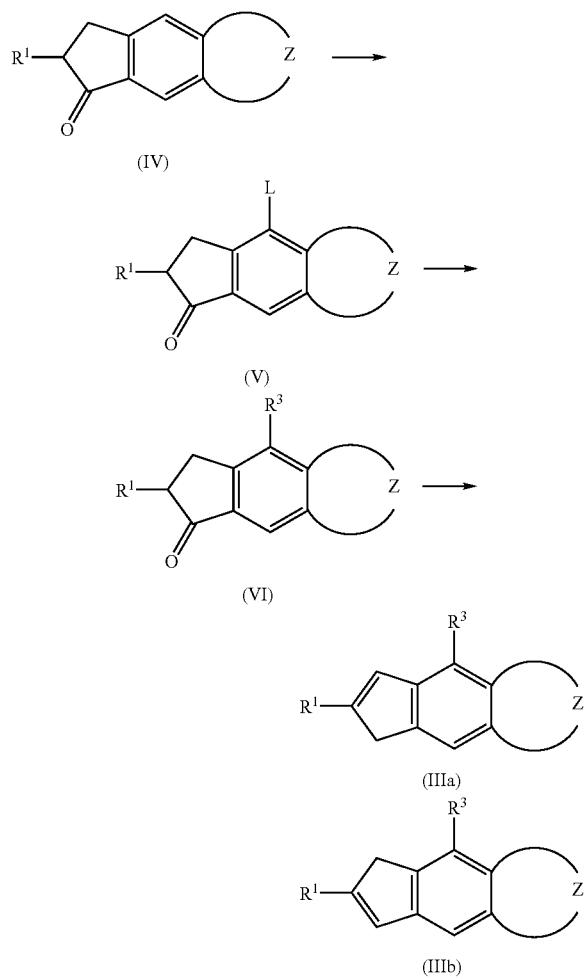

(IV)

(V)

(VI)

(IIIa)

(IIIb)

As an alternative, the indanone of the formula (V) can firstly be reacted to form an indene in which the leaving group L is subsequently replaced by a radical $R^3$ using a method analogous to that described in U.S. Pat. No. 5,789,634.

The novel organometallic transition metal compounds of the formula (I) act, particularly in the presence of suitable cocatalysts, as highly active catalyst constituents for the polymerization of olefins.

The cocatalyst which together with the novel organometallic transition metal compound of the formula (I) forms a polymerization-active catalyst system is able to convert the organometallic transition metal compound into a species which is polymerization-active toward at least one olefin. The cocatalyst is therefore sometimes also referred to as activating compound. The polymerization-active transition metal species is frequently a cationic species. In this case, the cocatalyst is frequently also referred to as cation-forming compound.

The present invention therefore further provides a catalyst system for the polymerization of olefins, which comprises at least one organometallic transition metal compound of the formula (I) and at least one cocatalyst which is able to convert the organometallic transition metal compound into a species which is polymerization-active toward at least one olefin.

Suitable cocatalysts or cation-forming compounds are, for example, compounds such as aluminoxanes, strong uncharged Lewis acids, ionic compounds having a Lewis-acid cation or anionic compounds containing Brönsted acids as cations. Preference is given to an aluminoxane as cocatalyst.

In the case of metallocene complexes as organometallic transition metal compounds, the cocatalysts are frequently also referred to as compounds capable of forming metallocenium ions.

As aluminoxanes, it is possible to use, for example, the compounds described in WO 00/31090. Open-chain or cyclic aluminoxane compounds of the formula (VII) or (VIII)

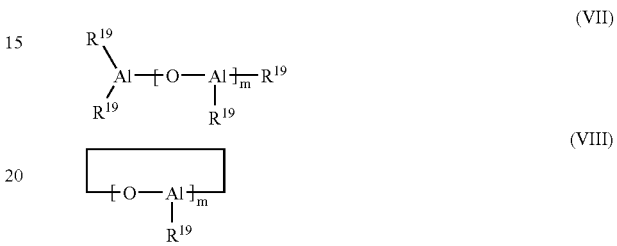

(VII)

(VIII)

where $R^{19}$ is a $C_1$-$C_4$-alkyl group, preferably a methyl or ethyl group, and m is an integer from 5 to 30, preferably from 10 to 25, are particularly useful.

These oligomeric aluminoxane compounds are usually prepared by reacting a solution of trialkylaluminum with water. In general, the oligomeric aluminoxane compounds obtained in this way are in the form of mixtures of both linear and cyclic chain molecules of various lengths, so that m may be regarded as a mean. The aluminoxane compounds can also be present in a mixture with other metal alkyls, preferably aluminum alkyls.

Furthermore, modified aluminoxanes in which some of the hydrocarbon radicals or hydrogen atoms have been replaced by alkoxy, aryloxy, siloxy or amide groups can also be used in place of the aluminoxane compounds of the formula (VII) or (VIII).

It has been found to be advantageous to use the novel organometallic transition metal compound of the formula (I) and the aluminoxane compounds in such amounts that the atomic ratio of aluminum from the aluminoxane compounds to the transition metal from the organometallic transition metal compound is in the range from 10:1 to 1 000:1, preferably in the range from 20:1 to 500:1 and in particular in the range from 30:1 to 400:1.

As strong, uncharged Lewis acids, preference is given to compounds of the formula (IX)

$$M^3X^1X^2X^3 \quad (IX)$$

where $M^3$ is an element of group 13 of the Periodic Table of the Elements, in particular B, Al or Ga, preferably B, $X^1$, $X^2$ and $X^3$ are each, independently of one another, hydrogen, $C_1$-$C_{10}$-alkyl, $C_6$-$C_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryl, preferably pentafluorophenyl.

Further examples of strong, uncharged Lewis acids are given in WO 00/31090.

Particular preference is given to compounds of the formula (IX) in which $X^1$, $X^2$ and $X^3$ are identical, preferably tris(pentafluorophenyl)borane.

Strong uncharged Lewis acids which are suitable as cocatalysts or cation-forming compounds also include the reaction products from the reaction of a boronic acid with two equivalents of a trialkylaluminum or the reaction products from the reaction of a trialkylaluminum with two equivalents of an acidic fluorinated, in particular perfluorinated, hydrocarbon compound such as pentafluorophenol or bis(pentafluorophenyl)borinic acid.

Suitable ionic compounds having Lewis-acid cations include salt-like compounds of the cation of the formula (X)

$$[(y^{a+})Q^1Q^2\ldots Q^z]^{d+} \qquad (X)$$

where

Y is an element of groups 1 to 16 of the Periodic Table of the Elements, $Q^1$ to $Q^z$ are each singly negatively charged groups such as the $C_1$-$C_{28}$-alkyl, $C_6$-$C_{15}$-aryl, alkylaryl, arylalkyl, haloalkyl, haloaryl each having from 6 to 20 carbon atoms in the aryl radical and from 1 to 28 carbon atoms in the alkyl radical, $C_3$-$C_{10}$-cycloalkyl which may bear $C_1$-$C_{10}$-alkyl groups as substituents, halogen, $C_1$-$C_{28}$-alkoxy, $C_6$-$C_{15}$-aryloxy, silyl or mercaptyl groups, a is an integer from 1 to 6 and z is an integer from 0 to 5, and d corresponds to the difference a–z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

Salts having noncoordinating anions can also be prepared by mixing a boron or aluminum compound, e.g. an aluminum alkyl, with a second compound which can react to link two or more boron or aluminum atoms, e.g. water, and a third compound which forms an ionizing ionic compound with the boron or aluminum compound, e.g. triphenylchloromethane. In addition, a fourth compound which likewise reacts with the boron or aluminum compound, e.g. pentafluorophenol, can be added.

Ionic compounds containing Brönsted acids as cations likewise preferably have noncoordinating counterions. As Brönsted acids, particular preference is given to protonated amine or aniline derivatives. Preferred cations are N,N-dimethylanilinium, N,N-dimethylcyclohexylammonium and N,N-dimethylbenzylammonium and also derivatives of the latter two.

Preferred ionic compounds as cocatalysts or cation-forming compounds are, in particular, N,N-dimethylanilinium tetrakis(pentafluorophenyl)borate, N,N-dimethylcyclohexylammonium tetrakis(pentafluorophenyl)borate and N,N-dimethylbenzylammonium tetrakis(pentafluorophenyl)borate.

It is also possible for two or more borate anions to be joined to one another, as in the dianion $[(C_6F_5)_2B\text{---}C_6F_4\text{---}B(C_6F_5)_2]^{2-}$, or the borate anion can be bound via a bridge having a suitable functional group to the surface of a support particle.

Further suitable cocatalysts or cation-forming compounds are listed in WO 00/31090.

The amount of strong, uncharged Lewis acids, ionic compounds having Lewis-acid cations or ionic compounds containing Brönsted acids as cations is usually from 0.1 to 20 equivalents, preferably from 1 to 10 equivalents, based on the novel organometallic transitional metal compound of the formula (I).

Further suitable cocatalysts or cation-forming compounds are boron-aluminum compounds such as di[bis(pentafluorophenylboroxy)]methylalane. Such boron-aluminum compounds are disclosed, for example, in WO 99/06414.

It is also possible to use mixtures of all the abovementioned cocatalysts or cation-forming compounds. Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane.

Preference is given to using both the novel organometallic transition metal compound of the formula (I) and the cocatalysts or cation-forming compounds in a solvent, in which case aromatic hydrocarbons having from 6 to 20 carbon atoms, in particular xylenes and toluene, are preferred.

The catalyst can further comprise a metal compound of the formula (XI), $$M^4(R^{20})_r(R^{21})_s(R^{22})_t \qquad (XI)$$

where $M^4$ is an alkali metal, an alkaline earth metal or a metal of group 13 of the Periodic Table, i.e. boron, aluminum, gallium, indium or thallium, $R^{20}$ is hydrogen, $C_1$-$C_{10}$-alkyl, $C_6$-$C_{15}$-aryl, alkylaryl or arylalkyl each having from 1 to 10 carbon atoms in the alkyl part and from 6 to 20 carbon atoms in the aryl part, $R^{21}$ and $R^{22}$ are identical or different and are each hydrogen, halogen, $C_1$-$C_{10}$-alkyl, $C_6$-$C_{15}$-aryl, alkylaryl, arylalkyl or alkoxy each having from 1 to 10 carbon atoms in the alkyl radical and from 6 to 20 carbon atoms in the aryl radical, r is an integer from 1 to 3, and s and t are integers from 0 to 2, with the sum r+s+t corresponding to the valence of $M^4$, where the metal compound of the formula (XI) is usually not identical to the cocatalyst or the cation-forming compound. It is also possible to use mixtures of various metal compounds of the formula (XI).

Among the metal compounds of the formula (XI), preference is given to those in which $M^4$ is lithium, magnesium or aluminum and $R^{21}$ and $R^{22}$ are each $C_1$-$C_{10}$-alkyl.

Particularly preferred metal compounds of the formula (XI) are n-butyllithium, n-butyl-n-octylmagnesium, n-butyl-n-heptylmagnesium, tri-n-hexylaluminum, triisobutylaluminum, triethylaluminum and trimethylaluminum and mixtures thereof.

When a metal compound of the formula (XI) is used, it is preferably present in the catalyst in such an amount that the molar ratio of $M^4$ from formula (XI) to transition metal $M^1$ from the novel organometallic transition metal compound of the formula (I) is from 800:1 to 1:1, in particular from 200:1 to 2:1.

Particular preference is given to a catalyst system comprising a novel organometallic transition metal compound of the formula (I) and at least one cocatalyst and additionally a support. To obtain such a supported catalyst system, the unsupported catalyst system can be reacted with a support. In principle, the order in which the support, the organometallic transition metal compound according to the present invention and the cocatalyst are combined is immaterial. The organometallic transition metal compound and the cocatalyst can be immobilized independently of one another or simultaneously. After the individual process steps, the solid can be washed with suitable inert solvents, e.g. aliphatic or aromatic hydrocarbons.

As supports, preference is given to using finely divided supports which can be any organic or inorganic, inert solids. In particular, the support can be a porous solid such as talc, a sheet silicate, an inorganic oxide or a finely divided polymer powder (e.g. polyolefin).

Suitable inorganic oxides may be found among the oxides of elements of groups 2, 3, 4, 5, 13, 14, 15 and 16 of the Periodic Table of the Elements. Examples of oxides preferred as supports include silicon dioxide, aluminum oxide, and also mixed oxides of the elements calcium, aluminum, silicon, magnesium or titanium and also corresponding oxide mixtures. Other inorganic oxides which can be used alone or in combination with the abovementioned preferred oxidic supports are, for example, MgO, $ZrO_2$, $TiO_2$ or $B_2O_3$. A preferred mixed oxide is, for example, calcined hydrotalcite.

The support materials used preferably have a specific surface area in the range from 10 to 1 000 $m^2$/g, a pore volume in the range from 0.1 to 5 ml/g and a mean particle size of from 1 to 500 µm. Preference is given to supports having a specific surface area in the range from 50 to 500 $m^2$/g, a pore volume in the range from 0.5 to 3.5 ml/g and a mean particle size in the range from 5 to 350 µm. Particular preference is given to supports having a specific surface area in the range from 200 to 400 $m^2$/g, a pore volume in the range from 0.8 to 3.0 ml/g and a mean particle size of from 10 to 100 µm.

The inorganic support can be subjected to a thermal treatment, e.g. to remove adsorbed water. Such a drying treatment is generally carried out at from 80 to 300° C., preferably from 100 to 200° C., with drying at from 100 to 200° C. preferably being carried out under reduced pressure and/or a blanket of inert gas (e.g. nitrogen), or the inorganic support can be calcined at from 200 to 1 000° C. to produce the desired structure of the solid and/or set the desired OH concentration on the surface. The support can also be treated chemically using customary desiccants such as metal alkyls, preferably aluminum alkyls, chlorosilanes or $SiCl_4$, or else methylaluminoxane. Appropriate treatment methods are described, for example, in WO 00/31090.

The inorganic support material can also be chemically modified. For example, treatment of silica gel with $(NH_4)_2SiF_6$ leads to fluorination of the silica gel surface, or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by means of appropriate purification and drying operations before use. It is also possible to use functionalized polymer supports, e.g. supports based on polystyrene, via whose functional groups, for example ammonium or hydroxy groups, at least one of the catalyst components can be immobilized.

In a preferred embodiment of the preparation of the supported catalyst system, at least one of the novel organometallic transition metal compounds of the formula (I) is brought into contact in a suitable solvent with at least one cocatalyst as activating or cation-forming compound, giving a soluble or insoluble, preferably soluble, reaction product, an adduct or a mixture.

The preparation obtained in this way is then mixed with the dehydrated or passivated support material, the solvent is removed and the resulting supported organometallic transition metal catalyst system is dried to ensure that the solvent is completely or mostly removed from the pores of the support material. The supported catalyst is usually obtained as a free-flowing powder. Examples of the industrial implementation of the above process are described in WO 96/00243, WO 98/40419 or WO 00/05277.

A further preferred embodiment comprises firstly immobilizing the cocatalyst or the cation-forming compound on the support material and subsequently bringing this supported cocatalyst or this cation-forming compound into contact with the organometallic transition metal compound according to the present invention.

Cocatalyst systems of significance therefore likewise include combinations which are obtained by combining the following components:

1st component: at least one defined boron or aluminum compound,

2nd component: at least one uncharged compound which has at least one acidic hydrogen atom, 3rd component: at least one support, preferably an inorganic oxidic support and optionally as 4th component a base, preferably an organic nitrogen-containing base such as an amine, an aniline derivative or a nitrogen heterocycle.

The boron or aluminum compounds used in the preparation of the supported cocatalysts are preferably compounds of the formula (XII)

(XII)

where the radicals $R^{23}$ are identical or different and are each hydrogen, halogen, $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl or an $OSiR^{24}{}_3$ group, where the radicals $R^{24}$ are identical or different and are each hydrogen, halogen, $C_1$-$C_{20}$-alkyl, $C_1$-$C_{20}$-halonalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, preferably hydrogen, $C_1$-$C_8$-alkyl or $C_7$-$C_{20}$-arylalkyl, and $M^5$ is boron or aluminum, preferably aluminum.

Particularly preferred compounds of the formula (XII) are trimethylaluminum, triethylaluminum and triisobutylaluminum.

The uncharged compounds which have at least one acidic hydrogen atom and can react with compounds of the formula (XII) are preferably compounds of the formula (XIII), (XIV) or (XV),

(XIII)

(XIV)

(XV)

where the radicals $R^{25}$ are identical or different and are each hydrogen, halogen, a boron-free organic radical having from 1 to 40 carbon atoms, e.g. $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, an $Si(R^{27})_3$ radical or a $CH(SiR^{27}{}_3)_2$ radical, where $R^{27}$ is a boron-free organic radical having from 1 to 40 carbon atoms, e.g. $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, and $R^{26}$ is a divalent organic group having from 1 to 40 carbon atoms, e.g. $C_1$-$C_{20}$-alkylene, $C_1$-$C_{20}$-haloalkylene, $C_6$-$C_{20}$-arylene, $C_6$-$C_{20}$-haloarylene, $C_7$-$C_{40}$-arylalkylene, $C_7$-$C_{40}$-haloarylalkylene, $C_7$-$C_{40}$-alkylarylene, $C_7$-$C_{40}$-haloalkylarylene, D is an element of group 16 of the Periodic Table of the Elements or an $NR^{26}$ group, where $R^{28}$ is hydrogen or a $C_1$-$C_{20}$-hydrocarbon radical such as $C_1$-$C_{20}$-alkyl or $C_6$-$C_{20}$-aryl, or is preferably oxygen, and h is 1 or 2.

Suitable compounds of the formula (XIII) include water, alcohols, phenol derivatives, thiophenol derivatives or aniline derivatives, with halogenated and especially perfluorinated alcohols and phenols being of particular importance. Examples of particularly useful compounds are pentafluorophenol, 1,1-bis(pentafluorophenyl)methanol and 4-hydroxy-2,2',3,3',4',5,5',6,6'-nonafluorobiphenyl.

Suitable compounds of the formula (XIV) include boronic acids and borinic acids, in particular borinic acids bearing perfluorinated aryl radicals, for example $(C_6F_5)_2BOH$.

Suitable compounds of the formula (XV) are dihydroxy compounds in which the divalent carbon-containing group is preferably halogenated, in particular perfluorinated. An example of such a compound is 4,4'-dihydroxy-2,2',3,3',5,5',6,6'-octafluorobiphenyl hydrate.

Examples of combinations of compounds of the formula (XII) with compounds of the formula (XIII) or (XV) are trimethylaluminum/pentafluorophenol, trimethylaluminum/1-bis(pentafluorophenyl)-methanol, trimethylaluminum/4-hydroxy-2,2',3,3',4',5,5',6,6'-nonafluorobiphenyl, triethylaluminum/pentafluorophenol, triisobutylaluminum/pentafluorophenol and triethylaluminum/4,4'-dihydroxy-2,2',3,3',5,5',6,6'-octafluorobiphenyl hydrate, giving, for example, reaction products of the following type.

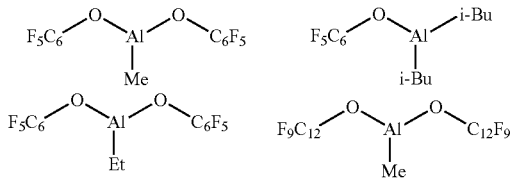

Examples of reaction products from the reaction of at least one compound of the formula (XII) with at least one compound of the formula (XIV) are:

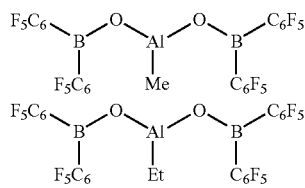

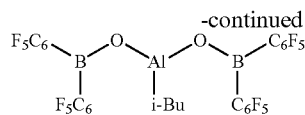

In principle, the components can be combined in any way.

If desired, the reaction products from the reaction of at least one compound of the formula (XII) with at least one compound of the formula (XIII), (XIV) or (XV) and optionally the organic nitrogen base are additionally combined with an organometallic compound of the formula (VII), (VIII), (IX) and/or (XI) to form, together with the support, the supported cocatalyst system.

In a preferred variant, the 1st component, e.g. compounds of the formula (XII), and the 2nd component, e.g. compounds of the formula (XIII), (XIV) or (XV), are mixed, a support as 3rd component and a base as 4th component are mixed separately and the two mixtures are subsequently reacted with one another, with the reaction preferably taking place in an inert solvent or suspension medium. The supported cocatalyst formed can be freed of the inert solvent or suspension medium before it is reacted with the novel organometallic transition metal compound of the formula (I) and, if desired, a metal compound of the formula (XI) to give the catalyst system.

It is likewise possible firstly to prepolymerize the catalyst solid with α-olefins, preferably linear $C_2$-$C_{10}$-1-alkenes and in particular ethylene or propylene, and then to use the resulting prepolymerized catalyst solid in the actual polymerization. The mass ratio of catalyst solid used in the prepolymerization to monomer polymerized onto it is usually in the range from 1:0.1 to 1:200.

Furthermore, a small amount of an olefin, preferably an α-olefin, for example vinylcyclohexane, styrene or phenyldimethylvinylsilane, as modifying component, an antistatic or a suitable inert compound such as a wax or oil can be added as additive during or after the preparation of the supported catalyst system. The molar ratio of additives to organometallic transition metal compound according to the present invention is usually from 1:1 000 to 1 000:1, preferably from 1:5 to 20:1.

The novel organometallic transition metal compounds of the formula (I) or the catalyst systems in which they are present are suitable for the polymerization or copolymerization of olefins.

The present invention therefore also provides a process for preparing polyolefins by polymerization or copolymerization of at least one olefin in the presence of a catalyst system comprising at least one of the novel organometallic transition metal compounds of the formula (I).

In general, the catalyst system is used together with a further metal compound of the formula (XI), which can be different from the metal compound or compounds of the formula (XI) used in the preparation of the catalyst system, for the polymerization or copolymerization of olefins. The further metal compound is generally added to the monomer or the suspension medium and serves to purify the monomer of substances which can adversely affect the catalyst activity. It is also possible to add one or more further cocatalytic or cation-forming compounds to the catalyst system in the polymerization process.

The olefins can be functionalized, olefinically unsaturated compounds such as ester or amide derivatives of acrylic or methacrylic acid, for example acrylates, methacrylates or acrylonitrile, or nonpolar olefinic compounds including aryl-substituted α-olefins.

Preference is given to polymerizing olefins of the formula R'''—CH=CH—R'', where R''' and R'' are identical or different and are each hydrogen or an organic radical, in particular a hydrocarbon radical having from 1 to 20 carbon atoms, in particular from 1 to 10 carbon atoms, or R''' and R'' together with the atoms connecting them can form one or more rings.

Examples of such olefins are 1-olefins having from 2 to 40, preferably from 2 to 10, carbon atoms, e.g. ethene, propene, 1-butene, 1-pentene, 1-hexene, 1-heptene, 1-octene, 1-decene or 4-methyl-1-pentene, or unsubstituted or substituted vinylaromatic compounds such as styrene and styrene derivatives or dienes such as 1,3-butadiene, 1,4-hexadiene, 1,7-octadiene, 5-ethylidene-2-norbornene, norbornadiene, ethylnorbornadiene or cyclic olefins such as norbornene, tetracyclododecene or methylnorbornene. Preference is given to ethene, propene, 1-butene, 1-hexene or 4-methyl-1-pentene.

The catalyst system of the present invention is particularly preferably used to homopolymerize propene or ethene or copolymerize ethene with $C_3$-$C_8$-α-olefins such as propene, 1-butene, 1-pentene, 1-hexene and/or 1-octene and/or cyclic olefins such as norbornene and/or dienes having from 4 to 20 carbon atoms, e.g. 1,4-hexadiene, norbornadiene, ethylidenenorbornene or ethylnorbornadiene, or most preferably to copolymerize propene with ethene and/or 1-butene. Examples of such copolymers are propene-ethene, propene-1-butene, ethene-1-hexene, ethene-1-octene copolymers and ethene-propene-ethylidenenorbornene or ethene-propene-1,4-hexadiene terpolymers.

The polymerization can be carried out in a known manner in bulk, in suspension, in the gas phase or in a supercritical medium in the customary reactors used for the polymerization of olefins. It can be carried out batchwise or preferably continuously in one or more stages. Solution processes, suspension processes, stirred gas-phase processes or gas-phase fluidized-bed processes are all possible. As solvent or suspension medium, it is possible to use inert hydrocarbons, for example isobutane, or else the monomers themselves.

The polymerization can be carried out at from −60 to 300° C. and pressures in the range from 0.5 to 3 000 bar. Preference is given to temperatures in the range from 50 to 200° C., in particular from 60 to 100° C., and pressures in the range from 5 to 100 bar, in particular from 15 to 70 bar. The mean residence times are usually from 0.5 to 5 hours, preferably from 0.5 to 3 hours. As molar mass regulator and/or to increase the activity, hydrogen can be used in the polymerization. Furthermore, customary additives such as antistatics can also be used. For the polymerization, the catalyst system of the present invention can be used directly, i.e. it is introduced in pure form into the polymerization system, or it is admixed with inert components such as paraffins, oils or waxes to improve meterability.

The novel organometallic transition metal compounds of the formula (I) or the catalyst systems in which they are present are very particularly useful for preparing polypropylene/propene-ethene copolymer mixtures.

The invention therefore further provides a process for preparing polypropylene/propene-ethene copolymer mixtures in the presence of a catalyst system as described above.

The polymers (hereinafter also (co)polymers) prepared using the catalyst system of the present invention display a uniform particle morphology and contain no fines. No deposits or cake material occur in the polymerization using the catalyst system of the present invention.

The (co)polymers obtainable using the catalyst system of the present invention include both homopolymers and random copolymers of propene. Their molar mass $M_w$ (measured by gel permeation chromatography) is in the range from 100 000 to 1 000 000 g/mol and their $M_w/M_n$ (measured by gel permeation chromatography) is in the range from 1.8 to 4.0, preferably from 1.8 to 3.5. Random copolymers of propene contain subordinate amounts of monomers which can be copolymerized with propene, for example $C_2$-$C_8$-alk-1-enes such as ethene, 1-butene, 1-pentene, 1-hexene or 4-methyl-1-pentene. It is also possible to use two or more different comonomers, which then gives, for example, random terpolymers.

The catalyst system of the present invention is particularly useful for preparing homopolymers of propene or copolymers of propene with up to 50% by weight of other copolymerized 1-alkenes having up to 8 carbon atoms. The copolymers of propene are random copolymers or block or high-impact copolymers. If the copolymers of propene have a random structure, they generally contain up to 50% by weight, preferably up to 15% by weight, particularly preferably up to 5% by weight, of other 1-alkenes having up to 8 carbon atoms, in particular ethene, 1-butene, 4-methyl-1-pentene or a mixture of ethene and 1-butene, ethene and 1-hexene or ethene and 4-methyl-1-pentene.

The copolymers prepared using the catalyst system of the present invention may also be block or high-impact copolymers of propene which are obtained by, in the first stage, preparing a propylene homopolymer or a random copolymer of propene with from 0.001 to 15% by weight, preferably from 0.01 to 6% by weight, of other 1-alkenes having up to 8 carbon atoms (e.g. ethene, 1-butene, 1-hexene, 1-octene, 4-methyl-1-pentene) and then, in the second stage, polymerizing a propene-ethene copolymer which has an ethene content of from 15 to 80% by weight and, if desired, further $C_4$-$C_8$-alk-1-enes (e.g. 1-butene, 1-hexene, 1-octene, 4-methyl-1-pentene) onto this. In general, the amount of propene-ethene copolymer (which may comprise 1-butene, 1-hexene, 1-octene, 4-methyl-1-pentene as further monomers) polymerized on is such that the copolymer produced in the second stage makes up from 3 to 60% by weight of the end product.

The propylene homopolymers and copolymers prepared using the catalyst system of the present invention have a content of meso-configured diads (measured by means of $^{13}$C-NMR spectroscopy, see examples) of at least 90%, preferably at least 95% and particularly preferably at least 97%.

Random copolymers which have been produced using single-site catalysts (e.g. metallocene catalysts) have a number of particular properties compared to, for example, copolymers produced by means of Ziegler-Natta catalysts and having a comparable comonomer content.

Thus, copolymers produced by means of single-site catalysts have a comonomer distribution which is uniform over their molar mass spectrum. Such a distribution can be determined, for example, by means of a coupled GPC-IR measurement.

In copolymers produced by means of single-site catalysts, the comonomers are randomly distributed, while in the case of copolymers produced by means of Ziegler-Natta catalysts, the comonomer tends to be incorporated in blocks even at low comonomer contents. The comonomer content fluctuates only to a small extent if the fractions comprise a sufficiently large proportion (at least 10%) of the total polymer. In the case of the copolymers prepared using catalyst systems according to the present invention, the comonomer content fluctuates by a maximum of 10%, preferably a maximum of 5%, particularly preferably a maximum of 1.5%, between the fractions representing a sufficiently large proportion.

Copolymers produced by means of single-site catalysts have a narrow molar mass distribution ex reactor (in general, $M_w/M_n$ is <=3.0). Copolymers produced by means of Ziegler-Natta catalysts have broader molar mass distributions ex reactor.

Furthermore, copolymers produced by means of single-site catalysts have a low proportion of soluble material. When 10 mol % of ethene has been incorporated, the proportion of ether-soluble material is less than 5% by weight.

In addition, a combination of the abovementioned features leads to the polymers (homopolymers and copolymers) prepared using the catalyst system of the present invention being eluted within a narrow temperature range in a TREF. In the case of the homopolymers and random copolymers prepared using the catalyst system of the present invention, from 80 to 100% by weight is eluted within a temperature range extending from 15° C. below to 15° C. above the temperature at which maximum elution occurs ("peak temperature"). The range preferably extends from 15° C. below to 10° C. above the peak temperature and particularly preferably from 10° C. below to 10° C. above the peak temperature.

The polymers (homopolymers and copolymers) prepared using the catalyst system of the present invention are suitable for producing hard and stiff shaped bodies, fibers, filaments, injection-molded parts, films, plates or large hollow bodies (e.g. pipes) having a high tensile strength. The shaped parts display, in particular, a high toughness, even at temperatures below 20° C., combined with a high stiffness.

Shaped bodies (e.g. injection-molded articles) comprising the block or high-impact copolymers prepared using the catalyst system of the present invention are generally produced by the customary injection-molding processes known to those skilled in the art and have a novel property combination of stiffness, toughness and transparency and also display little stress whitening.

The modulus of elasticity, as a measure of the stiffness of the copolymers prepared using the catalyst system of the present invention, measured in a tensile test in accordance with ISO 527 is generally in the range from 500 to 6 000 MPa, preferably in the range from 800 to 2 000 MPa, very particularly preferably in the range from 900 to 1 400 MPa.

The Charpy impact toughness, as a measure of the toughness of the copolymers prepared using the catalyst system of the present invention, measured in accordance with ISO 179-2/1 eU, is >200 $kJ/m^2$ at 23° C. and >200 $kJ/m^2$ at −20° C. Preference is given to no fracture of the test specimen being recorded at 23° C.

The haze, as complementary value to the transparency (% transparency+% haze=100%), determined in accordance with ASTM D 1003 of the copolymers prepared using the catalyst system of the present invention is preferably less than 40%, particularly preferably less than 30%.

The injection-molded articles produced from the above-described polymers generally contain customary additives known to those skilled in the art, e.g. stabilizers, lubricants and mold release agents, fillers, nucleating agents, antistatics, plasticizers, dyes, pigments or flame retardants, in customary amounts. In general, these are incorporated during granulation of the product obtained in powder form in the polymerization.

Customary stabilizers include antioxidants such as sterically hindered phenols, processing stabilizers such as phosphites or phosphonites, acid scavengers such as calcium stearate or zinc stearate or dihydrotalcite, sterically hindered amines or UV stabilizers. In general, the propylene copolymer compositions according to the present invention contain one or more of the stabilizers in amounts of up to 2% by weight.

Suitable lubricants and mold release agents are, for example, fatty acids, calcium or zinc salts of fatty acids, fatty acid amides or low molecular weight polyolefin waxes, which are usually used in concentrations of up to 2% by weight.

Possible fillers are, for example, talc, chalk or glass fibers which can usually be used in amounts of up to 50% by weight.

Suitable nucleating agents are, for example, inorganic additives such as talc, silica or kaolin, salts of monocarboxylic or polycarboxylic acids, e.g. sodium benzoate or aluminum tert-butylbenzoate, dibenzylidenesorbitol or its $C_1$-$C_8$-alkyl-substituted derivatives such as methyl-, ethyl- or dimethyldibenzylidenesorbitol, or salts of diesters of phosphoric acid, e.g. sodium 2,2'-methylenebis(4,6-di-tert-butylphenyl)phosphate. The nucleating agent content of the propylene polymer composition is generally up to 5% by weight.

Such additives are generally commercially available and are described, for example, in Gächter/Müller, Plastics Additives Handbook, 4th Edition, Hansa Publishers, Munich, 1993.

The invention is illustrated by the following nonlimiting examples:

EXAMPLES

General

The letter "c" at the beginning of an experiment number or designation of a substance denotes experiments or substances which are not according to the present invention and have been included for comparative purposes.

Preparation of the Catalyst:

0.206 mmol of a metallocene dichloride were added at room temperature to 4.33 mmol of MAO (30% strength solution in toluene, from Albemarle). The solution was allowed to stand overnight at room temperature and was subsequently diluted with 10.9 ml of toluene. The diluted solution was carefully added to 10 g of silica (Sylopol 948, calcined at 600° C., from Grace). Particular attention was paid to the colored solution being uniformly distributed over the support material. After 10 minutes, the flask containing the catalyst suspension was connected to a vacuum line and dried until the content of volatile material had been reduced to less than 5% by weight.

Polymerizations:

Homopolymerizations were carried out in a 10 l reactor charged with 3.5 kg of liquid propene. The reactor was made inert by means of nitrogen before being charged. 8 ml of a 20% strength by weight solution of triethylaluminum in Exxsol (from Witco) were introduced into the reactor and the mixture was stirred at 30° C. for 15 minutes. If hydrogen was added, its concentration was set to 0.5 standard liters per liter of liquid propylene. A suspension of the respective catalyst in 20 ml of Exxsol was introduced into the reactor. The reactor temperature was increased to 65° C. and maintained at this temperature for 60 minutes. The polymerizations were stopped by venting the reactor. The polymers were dried overnight under reduced pressure before being analyzed.

Copolymerizations were carried out in a 10 l reactor charged with 3.5 kg of liquid propylene. A 20% by weight solution of triethylaluminum in Exxsol (from Witco) was introduced into the reactor and the mixture was stirred at 30° C. for 15 minutes. A suspension of the respective catalyst in 20 ml of Exxsol was introduced into the reactor. Ethylene was introduced into the reactor (total of 160 g). The reactor temperature was increased to 65° C. and maintained at this temperature for 60 minutes. The pressure in the reactor was maintained at 32 bar by continuous addition of ethylene (about 47 g of further ethylene introduced). The polymerizations were stopped by venting the reactor. The polymers were dried overnight under reduced pressure before being analyzed.

General procedures for the handling and synthesis of air- and moisture-sensitive substances: The synthesis and handling of the organometallic compounds and the catalysts was carried out with exclusion of air and moisture under argon (glove box and Schlenk techniques). All solvents used were purged with argon and dried over molecular sieves before use. Tetrahydrofuran (THF), diethyl ether and toluene were dried over sodium/benzophenone, pentane was dried over sodium/benzophenone/triglyme and dichloromethane was dried over calcium hydride by refluxing for a number of hours, and the solvents were subsequently distilled off and stored over 4A molecular sieves.

Anhydrous aluminum trichloride, indane (95% pure) and 2-bromoisobutyryl bromide (98% pure) were procured from Aldrich Chemical Company.

Mass spectra were measured using a Hewlett Packard series 6890 instrument which was equipped with a series 5973 mass analyzer (EI, 70 eV).

NMR spectra of organic and organometallic compounds were recorded on a Varian Unity-300 NMR spectrometer at room temperature. The chemical shifts are reported relative to $SiMe_4$.

Determination of the Melting Point:

The melting point $T_m$ was determined by means of a DSC measurement in accordance with ISO Standard 3146 in a first heating phase at a heating rate of 20° C. per minute to 200° C., a dynamic crystallization at a cooling rate of 20° C. per minute down to 25° C. and a second heating phase at a heating rate of 20° C. per minute back to 200° C. The melting point was then the temperature at which the curve of enthalpy versus temperature measured in the second heating phase displayed a maximum.

Gel Permeation Chromatography:

Gel permeation chromatography (GPC) was carried out at 145° C. in 1,2,4-trichlorobenzene using a Waters 150C GPC apparatus. The evaluation of the data was carried out using the software Win-GPC from HS-Entwicklungsgesellschaft für wissenschaftliche Hard-und Software mbH, Ober-Hilbersheim. The columns were calibrated by means of polypropylene standards having molar masses ranging from 100 to $10^7$ g/mol. The mass average molar mass ($M_w$) and number average molar mass ($M_n$) of the polymers were determined. The Q value is the ratio of mass average molar mass ($M_w$) to number average molar mass ($M_n$).

Determination of the Viscosity Number (I.V.):

The viscosity number was determined in an Ubbelohde viscometer PVS 1 fitted with an S 5 measuring head (both from Lauda) in decalin at 135° C. To prepare the sample, 20 mg of polymer were dissolved in 20 ml of decalin at 135° C. for 2 hours. 15 ml of the solution were placed in the viscometer and the instrument carried out a minimum of three running-out time measurements until a consistent result had been obtained. The I.V. was calculated from the running-out times by means of the relationship I.V.=$(t/t_0-1)*1/c$, where t=mean of the running-out time of the solution, $t_0$=mean of the running-out time of the solvent, c: concentration of the solution in g/ml.

Examples

1. Dimethylsilanediyl-(6-methyl-4-(4'-tert-butylphenyl)-1,2,3,5-tetrahydro-s-indacen-7-yl)-(2-isopropyl-4-(4'-tert-butylphenyl)-1-indenyl)-zirconium dichloride (1)

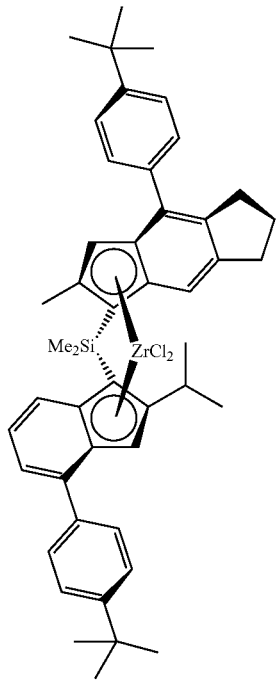

1a Preparation of 2-methyl-3,5,6,7-tetrahydro-s-indacen-1(2H)-one (1a)

50.71 g (377 mmol) of anhydrous aluminum trichloride were slowly added at 0° C. to a mixture of 19.3 g (163 mmol) of indane and 38.3 g of 2-bromoisobutyryl bromide in 500 ml of methylene chloride over a period of 30 minutes. The reaction mixture became dark red. The suspension was stirred at room temperature for 17 hours and subsequently poured onto 200 g of ice. The phases were separated. The organic phase was washed once with 200 ml of 1 normal hydrochloric acid, twice with 200 ml each time of saturated sodium hydrogencarbonate solution and twice with 200 ml each time of water. The organic phase was dried over anhydrous sodium sulfate and filtered. Removal of the solvent under reduced pressure gave 30 g (99% yield) of the compound (1a) as reddish brown oil. According to GC-MS, the content of (1a) in the oil was 99%.

1b Preparation of 4-bromo-2-methyl-3,5,6,7-tetrahydro-s-indacen-1(2H)-one (1 b)

31 g (162 mmol) of 2-methyl-3,5,6,7-tetrahydro-s-indacen-1(2H)-one (1a) were added to a suspension of 50 g (0.37 mol) of anhydrous aluminum trichloride in 200 ml of chloroform while stirring vigorously at 0° C. After stirring for one hour, a solution of 8 ml (160 mmol) of bromine in 20 ml of chloroform was added dropwise to the mixture at 0° C. and the mixture was subsequently stirred overnight. The reaction mixture was poured into 500 g of an ice/water mixture. The organic phase was separated off, washed with 5% strength sodium hydrogencarbonate solution and water and subsequently dried over magnesium sulfate. Filtration and removal of the solvent under reduced pressure gave 51 g of a red oil. GC-MS analysis indicated that the oil contained 84% of the desired compound (1b) and 14% of a dibromide by-product. The mixture was separated by column chromatography on silica gel using methylene chloride as eluant. This gave 18.7 g (44% yield) of the compound (1b).

$^1$H NMR ($d_1$-chloroform): 7.48 (s, 1H), 3.28 (dd, 1H), 2.98 (m, 4H), 2.74 (m, 1H), 2.59 (dd, 1H), 2.15 (t, 2H), 1.32 (d, 3H).

$^{13}$C NMR ($d_1$-chloroform): 208.19, 152.44, 151.81, 145.78, 137.09, 118.72, 117.84, 42.34, 35.48, 34.34, 33.19, 25.64, 16.24.

1c Preparation of 4-(4-tert-butylphenyl)-2-methyl-3,5,6,7-tetrahydro-s-indacen-1(2H)-one (1c)

0.3 g of palladium acetate (3 mol %) and 0.7 g of triphenylphosphine (6 mol %) were added to a well-stirred mixture of 12 g (0.045 mol) of 4-bromo-2-methyl-3,5,6,7-tetrahydro-s-indacen-1(2H)-one (1b), 11.2 g (0.063 mol) of tert-butylphenylboronic acid and 13.4 g (0.126 mol) of sodium carbonate in 170 ml of dimethoxyethane (DME)/56 ml of water. The reaction mixture was refluxed for 6 hours, poured into water and extracted with methylene chloride (5×100 ml). The combined organic phases were washed with sodium carbonate solution and water and dried over magnesium sulfate. After removal of the solvent, the crude product was chromatographed on silica gel (hexane/chloroform from 4/1 to 1/1). This gave 10 g (70% yield) of the compound (1c) as a viscous oil.

$^1$H NMR ($d_1$-chloroform): 7.59 (s, 1H), 7.46 (d, 8.3 Hz, 2H), 7.40 (d, 8.2 Hz, 2H), 3.21 (m, 1H), 2.99 (dd, 2H), 2.84 (dd, 2H), 2.69 (m, 1H), 2.56 (m, 1H), 2.07 (m, 2H), 1.38 (s, 9H), 1.26 (d, 7.2 Hz, 3H).

1d Preparation of 4-(4-tert-butylphenyl)-6-methyl-1,2,3,5-tetrahydro-s-indacene (1 d)

10 g (0.031 mol) of 4-(4-tert-butylphenyl)-2-methyl-3,5,6,7-tetrahydro-s-indacen-1(2H)-one (1c) were added dropwise at 0° C. to a solution of 0.6 g (0.016 mol) of lithium aluminum hydride in 100 ml of diethyl ether. The reaction mixture obtained was warmed to room temperature and stirred for a further one hour. 50 ml of 5% strength hydrochloric acid were added. The organic phase was separated off, washed twice with water and dried over magnesium sulfate. The residue was dissolved in 200 ml of benzene and, after addition of 0.5 g of p-toluenesulfonic acid, refluxed for 15 minutes. The solution was cooled to room temperature, washed with a 5% strength solution of sodium hydrogencarbonate and dried over magnesium sulfate. Evaporation of the solvent gave pure 4-(4-tert-butylphenyl)-6-methyl-1,2,3,5-tetrahydro-s-indacene in quantitative yield.

$^1$H NMR ($d_1$-chloroform): 7.41 (d, 8.2 Hz, 2H), 7.30 (d, 8.2 Hz, 2H), 7.10 (s, 1H), 6.45-6.43 (m, 1H), 3.29, 3.17 (s, 2H), 2.95 (dd, 2H), 2.78, 2.84 (dd, 2H), 2.06 (s, 3H), 2.02 (m, 2H), 1.36 (s, 9H).

1e Preparation of dimethylsilanediyl-(4-(4'-tert-butylphenyl)-6-methyl-1,2,3,5-tetrahydro-s-indacen-7-yl)(2-isopropyl-4-(4'-tert-butylphenyl)-1-indene) (1e)

6.5 g (21.5 mmol) of 4-(4'-tert-butylphenyl)-6-methyl-1,2,3,5-tetrahydro-s-indacene (1d) and 60 mg of copper(I) cyanide together with 200 ml of diethyl ether were placed in a reaction vessel and 10 ml (25 mmol) of a solution of n-butyllithium in hexane (2.5 molar) were added at −70° C. The reaction mixture was subsequently warmed to room temperature and stirred for a further one hour. The reaction mixture was cooled back down to −70° C. A solution of 8.5 g (22 mmol) of 2-isopropyl-7-(4'-tert-butyl-phenylyl)-1-indenyldimethylchlorosilane, which had been prepared by the method described in WO 01/48034, example 5, page 58, in 200 ml of diethyl ether was added over a period of one hour. The reaction mixture was stirred overnight at room temperature. 60 ml of water were added and the phases were separated. The organic phase was washed with 100 ml of water. The combined aqueous phases were extracted twice with a total of 100 ml of diethyl ether. The combined organic phases were dried over magnesium sulfate. After removal of the solvent, the residue was dried in an oil pump vacuum and 14 g of a viscous oil were isolated. The crude product was purified by chromatography on silica gel (hexane/chloroform 5/1). This gave 9 g (64% yield) of the ligand system (1e) as a mixture of double bond isomers in the form of a viscous oil.

$^1$H-NMR (400 MHz, CDCl$_3$): 7.51-7.15 (m, 12H), 6.85, 6.83 (s, 1H), 6.59, 6.57 (s, 1H), 4.01, 3.89, 3.68 (s, 2H), 2.95-2.85 (m, 4H), 2.75-2.63 (m, 1H), 2.22, 2.11 (s, 3H), 2.06-2.00 (m, 2H), 1.38, 1.39, 1.40 (s, 18H), 1.28-1.26 (d, 3H), 1.12-1.09 (d, 3H), −0.23, −0.22, −0.16 (s, 6H).

MS (direct): M$^+$=648 (C$_{47}$H$_{56}$Si)

1 Preparation of dimethylsilanediyl-(6-methyl-4-(4'-tert-butylphenyl)-1,2,3,5-tetrahydro-s-indacen-7-yl)(2-isopropyl-4-(4'-tert-butylphenyl)-1-indenyl)zirconium dichloride (1)

3.8 ml (9.6 mmol) of a solution of n-butyllithium in toluene (2.5 molar) were added at −70° C. to a solution of 3.1 g (4.8 mmol) of dimethylsilanediyl-(4-(4'-tert-butylphenyl)-6-methyl-1,2,3,5-tetrahydro-s-indacen-7-yl)(2-isopropyl-4-(4'-tert-butylphenyl)-1-indene) (1e) in 100 ml of diethyl ether. The reaction mixture was subsequently stirred at room temperature for 3 hours. The reaction mixture was cooled back down to −70° C. A suspension of 1.1 g (4.8 mmol) of zirconium tetrachloride in 50 ml of n-pentane was added and the reaction mixture was slowly warmed to room temperature and stirred overnight. The orange precipitate was separated off by filtration through a G3 reversible frit and washed with 10 ml of diethyl ether. The orange residue in the reversible frit was dried in an oil pump vacuum to give 3.2 g of the complex (1) in the form of a pseudo-rac/pseudo-meso mixture. Recrystallization from toluene gave 540 mg (14% yield) of the pseudo-rac compound (1).

$^1$H-NMR (400 MHz, CD$_2$Cl$_2$): 6.67 (d, 1H), 6.62-7.60 (m, 2H), 7.49-7.47 (m, 6H), 7.41 (s, 1H), 7.33 (d, 1H), 6.07 (dd, 1H), 6.98 (s, 1H), 6.65 (s, 1H), 3.36 (septet, 1H), 3.00-2.95 (m, 3H), 2.86-2.80 (m, 1H), 2.91 (s, 3H), 2.00 (m, 2H), 1.354, 1.347 (s, 18H), 1.34 (s, 6H), 1.11 (d, 3H), 1.05 (d, 3H).

2. Dimethylsilanediyl-(6-methyl-4-phenyl-1,2,3,5-tetrahydro-s-indacen-7-yl)-(2-isopropyl-4-(4'-tert-butylphenyl)-1-indenyl)-zirconium dichloride (2)

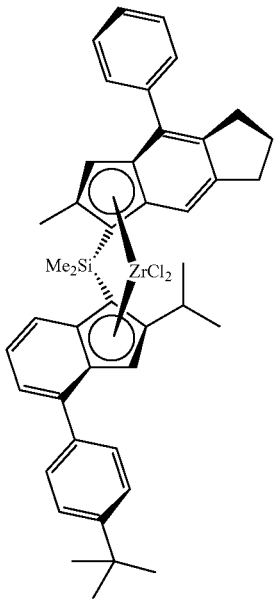

(2)

2a Preparation of 4-phenyl-2-methyl-3,5,6,7-tetrahydro-s-indacen-1(2H)-one (2a)

10 g (37.7 mmol) of 4-Bromo-2-methyl-3,5,6,7-tetrahydro-s-indacen-1(2H)-one (1b), 5.5 g (45.3 mmol) of phenylboronic acid, 8.8 g (80 mmol) of sodium carbonate, 80 ml of ethylene glycol and 12 ml of water were placed under a protective argon atmosphere and heated to 80° C. While stirring vigorously freshly prepared catalyst solution of 20 mg of palladium (II) acetate, 260 mg of 3,3',3''-phoshinidynetris(benzenesulfonic acid)trisodium salt (TPPTS) in 4 ml of water were added to the reaction and the reaction mixture was refluxed for 3 hrs. After cooling to room temperature, 40 ml of water was added and the ethylene glycol phase was extracted three times with a total of 240 ml of toluene. The combined organic phases were washed twice with a total of 250 ml of aqueous sodium chloride and dried over 150 g of sodium sulfate. Removal of solvents gave 9.6 g of brawn oil, which was gradually crystallized (97%, GC-MS).

$^1$H NMR (400 MHz, CDCl$_3$): 1.26 (d, 3H), 2.08 (m, 2H), 2.52 (dd, 1H), 2.68 (m, 1H), 2.81 (m, 2H), 3.00 (t, 2H), 3.17 (dd, 1H), 7.31 (d, 2H), 7.39 (dd, 1H), 7.45 (d, 2H), 7.61 (s, 1H)

2b Preparation of 4-phenyl-6-methyl-1,2,3,5-tetrahydro-s-indacene (2b)

9.6 g (24.4 mmol) of 4-phenyl-2-methyl-3,5,6,7-tetrahydro-s-indacen-1(2H)-one (2a) and 2.10 g (55 mmol) of sodium borohydride in 40 ml of toluene were placed in a reaction vessel. The solution was heated to 50° C. and 7 ml of methanol was added slowly and the reaction mixture was stirred at 50° C. for 3 hours. After cooling to room temperature 12 ml of water and 40 ml of 1 N sulfuric acid were added and the mixture was stirred for 30 minutes. After phase separation the water phase was extracted with toluene. Organic phase was evaporated and the residue was taken up in 100 ml of toluene and mixed with 100 mg of p-toluenesulfonic acid. Water was distilled off from this reaction mixture by refluxing for 2 hours on a water separator until reaction was complete. The reaction mixture was washed once with 100 ml of saturated sodium hydrogen carbonate solution and dried over magnesium sulfate. After removal of the solvent, the residue was dried in an oil pump vacuum. This gave 11.5 g of brawn oil. The crude product was purified by column chromatography (200 g of silica gel, 1 l of heptane: diethylether=9:1).

$^1$H NMR (400 MHz, CDCl$_3$): 2.04 (t, 2H), 2.08 (s, 3H), 2.77 (t, 2H), 2.97 (t, 2H), 3.15 (s, 2H), 6.47 (s, 1H), 7.13 (s, 1H), 7.35-7.48 (m, 5H)

2c Preparation of dimethylsilanediyl-(4-phenyl-6-methyl-1,2,3,5-tetrahydro-s-indacenyl)(2-i-propyl-4-(4-t-butylphenyl)-1-indenyl) (2c)

To 10.0 g (40.6 mmol) of 4-phenyl-6-methyl-1,2,3,5-tetrahydro-s-indacene (2b) and 135 mg (1.5 mmol) of copper cyanide (I) in 400 ml of diethylether was added dropwise at –70° C. 18.7 ml (45 mmol) of 2.5 M of n-butyllithium in n-hexane. The solution was slowly warmed to room temperature and stirred for 3 hrs at room temperature. Then to the solution was added at –70° C. 14 g (42.8 mmol) of chloro-(2-i-propyl-4-(4-t-butylphenyl)-indenyl)-dimethylsilane and the solution was warmed to room temperature and stirred for 5 hrs. The resulting back slurry solution was poured into an aqueous ammonium chloride solution and the organic layer was washed with brine, dried over sodium sulfate and the solvents were evaporated to give 23.6 g of crude product. This was purified by column chromatography (1200 g of silica gel, 12 l Heptane:CH$_2$Cl$_2$=5:1).

Yield: 17.8 g (74%)

$^1$H NMR (400 MHz, CDCl$_3$): –0.226, –0.157 (s, 6H), 1.10 (m, 3H), 1.25 (m, 3H), 1.393, 1.400 (s, 9H), 2.05 (m, 2H), 2.21 (s, 3H), 2.71 (septet, 1H), 2.86-2.96 (m, 4H), 3.65, 3.69, 3.90, 3.97 (s, 2H), 6.49, 6.53 (s, 1H), 6.81, 6.83 (s, 1H), 7.17-7.51 (m, 13H)

MS (direct): M$^+$=592 (C$_{43}$H$_{48}$Si)

2 Preparation of dimethylsilanediyl-(6-methyl-4-phenyl-1,2,3,5-tetrahydro-s-indacen-7-yl)-(2-isopropyl-4-(4'-tert-butylphenyl)-1-indenyl)-zirconium dichloride (2)

10.4 g (17.5 mmol) of dimethylsilanediyl-(4-phenyl-6-methyl-1,2,3,5-tetrahydro-s-indacenyl)(2-i-propyl-4-(4-t-butylphenyl)-1-indenyl) (2c) in 150 ml of diethyl ether were placed in a flask and added at –70° C. with 14 ml (35 mmol) of n-butyllithium solution (2.5 M in n-hexane). After the addition was complete, the mixture was stirred for 3 hours at room temperature. The reaction mixture was cooled to –70° C. and 4.1 g (17.5 mmol) of zirconium tetrachloride suspended in 100 ml of n-pentane was added. The reaction mixture was gradually warmed to room temperature and stirred at room temperature overnight. The orange precipitate was then separated off on a G3 frit and washed with 50 ml of n-pentane. The orange residue on the frit was dried in vacuum to give 5.5 g of crude complex (pseudo-rac/pseudo-meso=85%/15%, yield: 40%). Recrystallization from toluene gave 1.14 g of pure pseudo-rac-compound (2).

$^1$H NMR (400 MHz, CDCl$_3$): 1.07 (d, 3H), 1.10 (d, 3H), 1.32 (s, 6H), 1.37 (s, 9H), 2.00 (m, 2H), 2.20 (s, 3H), 2.82, 2.96 (m, 4H), 3.35 (septet, 1H), 6.65 (s, 1H), 7.01 (s, 1H), 7.06 (dd, 1H), 7.31 (t, 1H), 7.35 (d, 1H), 7.38 (s, 1H), 7.41 (t, 2H), 7.46 (d, 2H), 7.54 (broad, 2H), 7.62 (d, 1H), 7.64 (d, 2H)

MS (direct): M$^+$=750 (C$_{43}$H$_{46}$Cl$_2$SiZr)

3. Dimethylsilanediyl-(6-methyl-4-phenyl-1,2,3,5-tetrahydro-s-indacen-7-yl)-(2-isopropyl-4-phenyl-1-indenyl)zirconium dichloride (3)

(3)

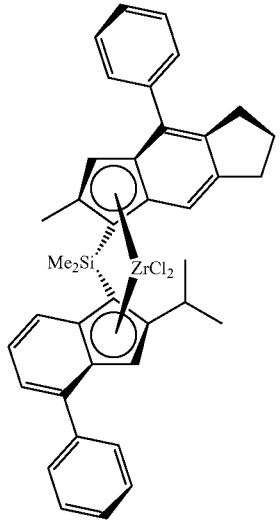

3a Dimethyl-(4-phenyl-6-methyl-1,2,3,5-tetrahydro-s-indacenyl)(2-i-propyl-4-phenyl-1-indenyl)-silane (3a)

To 12.3 g (50 mmol) of 4-phenyl-6-methyl-1,2,3,5-tetrahydro-s-indacene (2b) and 150 mg (1.5 mmol) of copper cyanide (I) in 450 ml of diethylether was added dropwise at −70° C. 23 ml (57 mmol) of 2.5 M of n-butyllithium in n-hexane. The solution was slowly warmed to room temperature and stirred for 3 hrs at room temperature. Then to the solution was added at −70° C. 16.4 g (50 mmol) of chloro-(2-i-propyl-4-phenyl-indenyl)-dimethylsilane and the solution was warmed to room temperature and stirred for 5 hrs. The resulting back slurry solution was poured into an aqueous ammonium chloride solution and the organic layer was washed with brine, dried over sodium sulfate and the solvents were evaporated to give 28 g of crude product. This was purified by column chromatography (800 g of silica gel, 101 Heptane:$CH_2Cl_2$=5:1). Yield: 9.5 g (35%)

$^1$H NMR (400 MHz, $CDCl_3$): −0.21, −0.17, −0.13 (s, 6H), 1.10 (m, 3H), 1.24 (m, 3H), 2.05 (m, 2H), 2.22 (s, 3H), 2.71 (m, 1H), 2.80-2.98 (m, 4H), 3.67, 3.68, 3.90, 3.99 (s, 2H), 6.49, 6.54 (s, 1H), 6.78 (s, 1H), 7.16-7.57 (m, 14H)

MS (direct): $M^+$=536 ($C_{39}H_{40}Si$)

3 Dimethylsilanediyl-(6-methyl-4-phenyl-1,2,3,5-tetrahydro-s-indacen-7-yl)-(2-isopropyl-4-phenyl-1-indenyl)-zirconium dichloride (3)

4.32 g (8.05 mmol) of dimethyl-(4-phenyl-6-methyl-1,2,3,5-tetrahydro-s-indacenyl)(2-i-propyl-4-phenyl-1-indenyl)-silane (3a) in 150 ml of diethyl ether were placed in a flask and added at −70° C. with 6.4 ml (16.1 mmol) of n-butyllithium solution (2.5 M in n-hexane). After the addition was complete, the mixture was stirred for 3 hours at room temperature. The reaction mixture was cooled to −70° C. and 1.9 g (8.05 mmol) of zirconium tetrachloride suspended in 100 ml of n-pentane was added. The reaction mixture was gradually warmed to room temperature and stirred at room temperature overnight. The orange precipitate was separated off on a G3 frit and washed with 50 ml of n-pentane. The orange residue on the frit was dried in vacuum to give 2.5 g of solid powder (rac/meso=89%/11%, yield: 42%). The product was re-crystallized in toluene to give pseudo-rac compound (3).

$^1$H NMR (400 MHz, $CDCl_3$): 1.05 (d, 3H), 1.11 (d, 3H), 1.32 (s, 6H), 1.99 (m, 2H), 2.20 (s, 3H), 2.82 (m, 1H), 2.95 (m, 3H), 3.34 (septet, 1H), 6.65 (s, 1H), 6.96 (s, 1H), 7.07 (dd, 1H), 7.31 (t, 1H), 7.34 (t, 1H), 7.35 (d, 1H), 7.38 (s, 1H), 7.42 (m, 4H), 7.53 (broad, 2H), 7.64 (d, 1H), 7.67 (d, 2H)

MS (direct): $M^+$=694 ($C_{39}H_{38}Cl_2SiZr$)

4. Dimethylsilanediyl-(2-methyl-4-(4-t-butylphenyl)-tetrahydrocyclopenta[b]naphthalene)-(2-isopropyl-4-(4'-tert-butylphenyl)-1-indenyl)-zirconium dichloride (4)

(4)

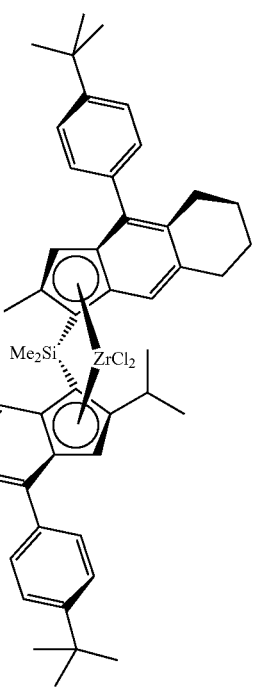

4a Preparation of 2-methyl-2,3,5,6,7,8-hexahydro-1H-cyclopenta[b]naphthalen-1-one (4a)

Methacryl chloride (37.5 ml, 375 mmol) was added at −70° C. to well-stirred suspension of $AlCl_3$ (100 g, 750 mmol) in $CH_2Cl_2$ (600 ml). After 20 min tetrahydronaphthalene (49.5 g, 375 mmol) was added. Reaction mixture was allowed to warm to room temperature, stirred for 16 h and poured into ice water-HCl (1 l/150 ml). Organic layer was separated, water layer was extracted by $CH_2Cl_2$ (2100 ml). Combined organic phases were washed by water, aq. $NaHCO_3$, dried over $MgSO_4$ and evaporated. Vacuum distillation (130-140° C./0.5 Torr) a mixture of ketones. After storage within 5 days desired isomer stays liquid and can be separated by decantation. The yield 30 g (40%).

4b Preparation of 4-bromo-2-methyl-2,3,5,6,7,8-hexahydro-1H-cyclopenta[b]naphthalen-1-one (4b)

2-Methyl-2,3,5,6,7,8-hexahydro-1H-cyclopenta[b]naphthalen-1-one (3a, 30 g, 150 mmol) in $CH_2Cl_2$ (50 ml) was added at −20° C. to the suspension of $AlCl_3$ (40 g, 300 mmol) in $CH_2Cl_2$ (250 ml). After 20 min of stirring, $Br_2$ (7.7 ml, 150 mmol) was added. Reaction mixture was allowed to warm to room temperature, stirred for 16 h, poured into ice water/HCl (500 ml/70 ml). Organic phase was separated, water phase was extracted by CH$_2$Cl$_2$ (two times 50 ml), combined organic fractions were washed by water, aq. KHCO$_3$, dried over MgSO$_4$ and evaporated. The residue was distilled in vacuo (175-180° C./0.5 Torr) yielding 31 g (74%) of product.

4c Preparation of 4-(4-t-butylphenyl)-2-methyl-2,3,5,6,7,8-hexahydro-1H-cyclopenta[b]naphthalen-1-one (4c)

Pd(OAc)$_2$ (0.74 g, 3 mol. %) and PPh$_3$ (1.73 g, 6 mol. %) were added to well stirred mixture of 2-methyl-2,3,5,6,7,8-hexahydro-1H-cyclopenta[b]naphthalen-1-one (4b, 31 g, 110 mmol), tert-butylphenylboronic acid (26.7 g, 150 mmol) and Na$_2$CO$_3$ (31.8 g, 300 mmol) in DME (380 ml)/H$_2$O (130 ml). The resulting mixture was refluxed with stirring for 6 h, cooled, poured into water (700 ml) and extracted by benzene (4 times of 100 ml). Resulting solution was filtered and evaporated. The product was obtained by column chromatography (silica gel 60, hexane/CH$_2$Cl$_2$ 1:1). The yield was 18.3 g (50%).

4d Preparation of 9-(4-tert-Butylphenyl)-2-methyl-5,6,7,8-tetrahydro-1H-cyclopenta[b]naphthalene (4d)

LiAlH$_4$ (0.95 g, 25 mmol) was added at −20° C. to the solution of 4-(4-tert-Butylphenyl)-2-methyl-2,3,5,6,7,8-hexahydro-1H-cyclopenta[b]naphthalen-1-one (16.6 g, 50 mmol) in Et$_2$O (150 ml). Resulting mixture was allowed to warm to room temperature and stirred for additional 1 h. Then 5% HCl (100 ml) was added, the resulting mixture was extracted by Et$_2$O (3 times of 50 ml). Combined organic phases were washed by water, dried over MgSO$_4$ and evaporated. Benzene (300 ml) and p-TSA (0.5 g) were added, and resulting solution was refluxed with Dean Stark head (control by TLC, benzene/EtOAc 4:1) within 4 h. Then the resulting solution was washed by water, aq. KHCO$_3$, water, dried over MgSO$_4$, passed through silica gel and evaporated giving 12.8 g (81%) of product.

4e Preparation of [4-(4-t-butylphenyl)-2-isopropyl-1H-inden-1-yl][4-(4-tert-butylphenyl)-2-methyl-5,6,7,8-tetrahydro-1H-cyclopenta[b]naphthalen-1-yl]dimethylsilane (4e)

Solution of 9-(4-tert-butylphenyl)-2-methyl-5,6,7,8-tetrahydro-1H-cyclopenta[b]naphthalene (4d, 2.97 g, 9.38 mmol) in Et$_2$O (50 ml) was cooled to −60° C., and n-BuLi (1.6 M in hexane, 6.04 ml, 9.67 mmol) was added. The resulting mixture was allowed to warm to room temperature, stirred for 3 h, cooled to −60° C., and CuCN (50 mg, 0.55 mmol) was added. After 15 min, solution of chloro-(4-(4-tert-butylphenyl)-2-isopropyl-1H-inden-1-yl)-dimethylsilane (9.67 mmol) in Et$_2$O (24 ml) was added, and resulting mixture was allowed to warm to room temperature and stirred for 16 h. Water (5 ml) and hexane (200 ml) were added, organic phase was separated, dried over MgSO$_4$, passed through silica gel and evaporated. The product was dried in vacuo and used without purification.

$^1$H NMR (CDCl$_3$, 20° C.): 7.66-7.22 (group of m, 12H, CAr—H); 6.94 (bs); 6.92 (bs); 6.41 (bs); 6.39 (bs) {2H, —CH=}; 4.13 (s); 4.09 (s); 4.02 (s); 3.95 (s) {2H, >CH—Si}; 2.39 (s); 2.29 (s) {3H, >C—CH3}; 3.00-2.66 (group of m); 1.95-1.75 (group of m); 1.36-1.14 (group of m) {9H, —CHMe, and —CH$_2$CH$_2$CH$_2$CH$_2$—}; 1.52-1.35 (group of s and d, 24H, —CH(CH$_3$)$_2$ and —C(CH$_3$)$_3$); 0.12-0.10 (group of s, 6H, Si-CH$_3$). Compound contains allyl-vinyl isomers.

4 Dimethylsilanediyl-(2-methyl-4-(4-t-butylphenyl)-tetrahydrocyclopenta[b]naphthalene)-(2-isopropyl-4-(4'-tert-butylphenyl)-1-indenyl)-zirconium dichloride (4)

Obtained [4-(4-tert-butylphenyl)-2-isopropyl-1H-inden-1-yl][4-(4-tert-butylphenyl)-2-methyl-5,6,7,8-tetrahydro-1H-cyclopenta[b]naphthalen-1-yl]dimethylsilane (4e, 5.82 g, 8.78 mmol) was dissolved in Et$_2$O (60 ml), cooled to −40° C., and n-BuLi (1.6M in hexane, 11.52 ml, 18.44 mmol) was added. Reaction mixture was allowed to warm to room temperature, stirred for 3 h, and evaporated. Residue was suspended in pentane (100 ml), cooled to −60° C., and ZrCl$_4$ (2.15 g, 9.22 mmol) was added. After 5 min Et$_2$O (1 ml) was added. Resulting mixture was allowed to warm to room temperature, stirred for additional 16 h, and filtered. Resulting orange-yellow powder was dried, DME (100 ml) and LiCl (0.3 g) were added, and the mixture was refluxed with stirring for 6 h. The product was obtained by subsequent recrystallization from DME and CH$_2$Cl$_2$/Et$_2$O. The yield of rac-form was 0.88 g (24.4%).

$^1$H NMR (CDCl$_3$, 20° C.): 7.67-7.04 (group of m, 12H, CAr—H); 7.03 (s, 1H); 6.47 (s, 1H) {C5 ring-H}; 3.48 (m, 4H); 1.12 (m; 4H) {8H, —CH$_2$CH$_2$CH$_2$CH$_2$—}; 2.77 (m, 1H, —CHMe$_2$); 2.18 (s, 3H, C—CH$_3$); 1.35 (bs 18H, —C(CH$_3$)$_3$); 1.34 (s, 3H); 1.33 (s, 3H) {Si—CH$_3$}; 1.13-1.10 (dd, 6H, —CH(CH$_3$)$_2$).

5. Dimethylsilanediyl-(6-methyl-4,8-diphenyl-1,2,3,5-tetrahydro-s-indacen-7-yl)-(2-isopropyl-4-(4'-tert-butylphenyl)-1-indenyl)-zirconium dichlorde (5)

(5)

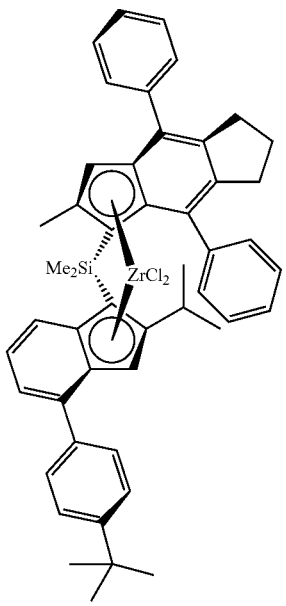

5a Preparation of 4,8-dibromo-2-methyl-3,5,6,7-tetrahydro-s-indacen-1(2H)-one (5a)

Suspension of 73.2 g AlCl$_3$ (0.542 mol) in 290 ml of chloroform was treated with 45 g (240 mmol) of 2-methyl-3,5,6,7-tetrahydro-s-indacen-1(2H)-one (1a) in 150 ml of chloroform at 0° C. under vigorous stirring. After stirring at 0° C. for 1 hr, the mixture was treated dropwisely with 24 ml (0.48 mol) of bromine in 50 ml of chloroform for 10 min at 0° C., cooling bath was removed and the solution was stirred overnight. The reaction mixture was poured into ice water and extracted with methylene chloride. Organic layer was isolated, washed with aq. NaHCO3 and water and was dried over MgSO$_4$. The solution was evaporated to dryness under vacuum to give 93 g of dark oil, which was gradually crystallized. This crude product was suspended in 100 ml of n-heptane and stirred for 1 hr at room temperature and filtered. 52 g of brown solid was obtained and it was determined by GC-MS to contain almost 100% of target compound (Yield: 63%). The filtrate was concentrated and the same procedure was repeated to get 10 g of the solid (totally 62 g, Yield: 75%).

$^1$H NMR (400 MHz, CDCl$_3$): 1.31 (d, 3H), 2.16 (pent., 2H), 2.53 (dd, 1H), 2.75 (m, 1H), 3.07 (m, 4H), 3.22 (dd, 1H)
$^{13}$C NMR (100 MHz, CDCl$_3$): 16.47, 23.31, 34.73, 34.92, 35.77, 43.34, 115.51, 118.08, 133.90, 147.09, 152.70, 154.64, 205.54

5b Preparation of 2-methyl-4,8-phenyl-3,5,6,7-tetrahydro-s-indacen-1(2H)-one (5b)

Into 20 g (0.312 mol) of KOH in 80 ml of water, were added 18.4 g (53 mmol) of 4,8-dibromo-2-methyl-3,5,6,7-tetrahydro-s-indacen-1(2H)-one (5a) in 400 ml of dimethoxyethane, 19.0 g (0.156 mol) of phenylboronic acid and 2.3 g (9 mmol) of triphenylphosphine and stirred by mechanical stirrer. The reaction mixture was vacuumed and filled with argon and then 0.6 g (2.67 mmol) of palladium (II) acetate was added and then the mixture was stirred at 90° C. for 4 hrs under argon atmosphere. Then it was cooled to room temperature and poured into 1 L of ice water, extracted with totally 600 ml of methylene chloride and organic phase was washed with water to become neutral, dried and evaporated to get 22 g of dark solid. The crude product was purified with column chromatography (silica gel, methylene chloride) to give 17.4 g of brown solid (Yield: 97%).

$^1$H NMR (400 MHz, CDCl$_3$): 1.22 (d, 3H), 2.02 (pent., 2H), 2.53 (dd, 1H), 2.64 (m, 1H), 2.86 (m, 4H), 3.18 (dd, 1H), 7.34-7.50 (m, 10H)
$^{13}$C NMR(100 MHz, CDCl$_3$): 16.35, 25.80, 31.98, 33.10, 33.75, 43.07, 127.33, 127.47, 127.63, 127.78, 127.93, 128.37, 128.57, 128.87, 128.98, 129.08, 131.99, 135.46, 135.97, 137.34, 138.25, 143.83, 150.15, 151.61

5c Preparation of 6-methyl-4,8-diphenyl-1,2,3,5-tetrahydro-s-indacene (5c)

17.4 g (51 mmol) of 2-methyl-4,8-diphenyl-3,5,6,7-tetrahydro-s-indacen-1(2H)-one (4b) and 3.8 g (100 mmol) of sodium borohydride in 100 ml of toluene were placed in a reaction vessel. The solution was heated to 50° C. and 22 ml of methanol was slowly added and the reaction mixture was stirred at 50° C. for 3 hours and then at room temperature overnight. During stirring solids were precipitated. 12 ml of water and 80 ml of 1 N sulfuric acid were added and the mixture was stirred at 35° C. for 30 minutes. 200 ml of methylene chloride was added and organic phase was separated and evaporated and the residue (18.0 g) was taken up in 200 ml of toluene and mixed with 100 mg of p-toluenesulfonic acid. Water was distilled off from this reaction mixture by refluxing for 1 hour on a water separator until reaction was complete. The reaction mixture was washed once with 100 ml of saturated sodium hydrogen carbonate solution and dried over magnesium sulfate. After removal of the solvent, the residue was dried in an oil pump vacuum. This gave 18 g of pale brawn solid. The crude product was purified by column chromatography.

$^1$H NMR (400 MHz, CDCl$_3$): 2.00 (t, 2H), 2.04 (s, 3H), 2.84 (t, 2H), 2.90 (t, 2H), 3.24 (s, 2H), 6.44 (s, 1H), 7.35 (m, 2H), 2.44 (m, 8H)
$^{13}$C NMR (100 MHz, CDCl$_3$): 145.67, 143.03, 141.06, 140.58, 140.30, 139.92, 138.54, 133.45, 129.67, 129.54, 128.86, 128.24, 128.06, 126.83, 126.61, 126.27, 42.49, 32.75, 32.50, 31.89, 31.45, 26.14, 16.77

5d Preparation of dimethyl-(6-methyl-4,8-diphenyl-1,2,3,5-tetrahydro-s-indacenyl)(2-i-propyl-4-(4-t-butylphenyl)-1-indenyl)-silane (5d)

To 11.4 g (35.3 mmol) of 6-methyl-4,8-diphenyl-1,2,3,5-tetrahydro-s-indacene (5c) and 100 mg of copper cyanide (I) in 300 ml of diethylether plus 20 ml of THF was added dropwise at −70° C. 16 ml (40 mmol) of 2.5 M of n-butyllithium in n-hexane. The solution was slowly warmed to room temperature and stirred for 3 hrs at room temperature (yellow brown suspension). Then to the suspension was added at −70° C. 13.4 g (35 mmol) of chloro-(2-i-propyl-4-(4-t-butylphenyl)-indenyl)-dimethylsilane and the solution was warmed to room temperature and stirred over the weekend. The resulting brown slurry solution was poured into an aqueous ammonium chloride solution and the organic layer was washed with brine, dried over sodium sulfate and the solvents were evaporated. The crude product was purified by column chromatography to get 17.0 g of amorphous solid (yield: 64%).

$^1$H NMR: (400 MHz, CDCl$_3$): isomer mixtures, −0.69, −0.66, −0.64, −0.51 (each s, 6H), 0.99 (d, 3H), 1.10, 1.21 (each d, 3H), 1.37, 1.38 (each s, 9H), 1.94, 2.09 (m, 2H), 2.06, 2.13 (each s, 3H), 2.35, 2.50, 2.60 (each m, 2H), 2.92 (m, 2H), 2.96, 3.05 (each s, 1H, allyl), 3.19 (m, 1H), 4.26, 4.34 (each s, 1H, allyl), 6.50, 6.61, 6.64 (each s, 2H, vinyl), 7.12-7.62 (m, 17H)
MS (direct): M$^+$=669 (C$_{49}$H$_{52}$Si)

5 Dimethylsilanediyl-(6-methyl-4,8-diphenyl-1,2,3,5-tetrahydro-s-indacen-7-yl)-(2-isopropyl-4-(4'-tert-butylphenyl)-1-indenyl)-zirconium dichloride (5)

7.63 g (11.4 mmol) of (5d) together with 100 ml of diethyl ether were placed in a flask and added at −70° C. with 9.1 ml (22.8 mmol) of n-butyllithium solution (2.5 M in toluene). After the addition was complete, the mixture was stirred for 3 hours at room temperature. The reaction mixture was cooled to −70° C. and 2.66 g (11.4 mmol) of zirconium tetrachloride suspended in 60 ml of n-pentane was added. The reaction mixture was gradually warmed to room temperature and stirred at room temperature over the weekend. The orange precipitate was then separated off on a G3 frit and washed with 10 ml of n-pentane. The orange residue on the frit was dried in vacuum to give 6.7 g of crude metallocene (5) (pseudo-rac/pseudo-meso=61%/39%, yield: 67%). Recrystallization from toluene gave 350 mg of the pseudo-rac compound (5).

$^1$H NMR (400 MHz, CD$_2$Cl$_2$): −0.115 (s, 3H), 0.87 (d, 3H), 1.16 (d, 3H), 1.18 (s, 3H), 1.35 (s, 9H), 1.75 (m, 1H), 2.01 (m, 1H), 2.28 (s, 3H), 2.49 (m, 1H), 2.89 (m, 1H), 3.02 (m, 1H), 3.09 (m, 2H), 6.79 (s, 1H), 7.04 (dd, 1H), 7.06 (s, 1H), 7.33 (m, 2H), 7.38-7.55 (m, 12H), 7.65 (m, 2H)
MS (direct): M$^+$=826 (C$_{49}$H$_{50}$Cl$_2$SiZr)

6. Dimethylsilanediyl-(6-methyl-4-(2,5-dimethylphenyl)-1,2,3,5-tetrahydro-s-indacen-7-yl)-(2-isopropyl-4-(4'-tert-butylphenyl)-1-indenyl)-zirconium dichloride (6)

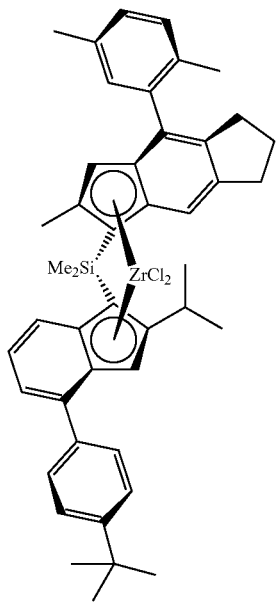

(6)

6a Preparation of 2-methyl-4-(2,5-dimethylphenyl)-3,5,6,7-tetrahydro-s-indacen-1(2H)-one (6a)

A mixture containing 30.0 g (107.5 mmol)) of 4-bromo-2-methyl-3,5,6,7-tetrahydro-2H-s-indacen-1-one, 410 ml of dimethoxyethane, 21.0 g (135.8 mmol) of 2,5-dimethylphenyl boronic acid, 20.0 g (321 mmol) of potassium hydroxide and 72 ml of water was degassed and the flask atmosphere replaced with nitrogen. Stirring was initiated and 0.60 g (2.7 mmol) of palladium acetate and 2.4 g (9.1 mmol) of triphenylphosphine were added. The reaction mixture was stirred at 78° C. for 4 h. After cooling, the mixture was poured into water and the organic phase was separated. The aqueous phase was extracted two times with 200 ml of dichloromethane. The combined organic fractions were dried and solvents removed on a rotoevaporator giving 45 g of crude product. The crude product was dissolved in dichloromethane and filtered through a plug of silica gel to give 24 g of target compound as an oil after evaporation of the solvent (77% yield based on the indacen-1-one starting material).

EIMS: m/z (%) 290 (M$^+$, 100), 269 (92), 247 (43), 226 (31), 203 (22), 165 (8).

6b Preparation of 6-methyl-4-(2,5-didmethylphenyl)-1,2,3,5-tetrahydro-s-indacene (6b)

4-(2,5-Dimethyl-phenyl)-2-methyl-3,5,6,7-tetrahydro-2H-s-indacen-1-one (24.0 g, 0.0806 mol) was dissolved in 300 ml of methyl-tert-butylether and treated with 46 ml of an ether solution of LiAlH4 (1 M, 0.046 mol) at 0° C. After stirring at room temperature for 2 h, 20 ml of a 2 M HCl solution was added cautiously. The organic phase was separated and the water phase was extracted two times with methyl-tert-butylether. The combined organic fractions were dried (MgSO$_4$) and evaporated to an oil. The oil was dissolved in toluene (200 ml), p-toluenesulfonic acid (0.5 g) was added, and the mixture was stirred at reflux for 1 h. After cooling, the reaction mixture was washed with a saturated aqueous solution of NaHCO$_3$, with brine solution and was dried (MgSO$_4$). Evaporation of solvent gave 20.4 g of product (92% yield).

$^1$H NMR (CDCl$_3$): 7.0-7.3 (m, 3H), 6.9 (s, 1H), 6.5 (s, 1H), 3.1-2.8 (m, 3H), 2.4-2.7 (m, 2H), 2.3 (s, 3H), 2.0-2.2 (m, 2H), 2.1 (s, 3H), 2.0 (s, 3H).

EIMS: m/z (%) 274 (M$^+$, 100), 258 (43), 231 (29), 215 (25), 189 (8), 169 (9), 152 (8).

6c Preparation of dimethyl-(4-(2,5-dimethylphenyl)-6-methyl-1,2,3,5-tetrahydro-s-indacenyl)(2-i-propyl-4-(4-t-butylphenyl)-1-indenyl)-silane (6c)

4-(2,5-Dimethyl-phenyl)-6-methyl-1,2,3,5-tetrahydro-s-indacene (3.3 g, 12.1 mmol) was dissolved in 50 ml of ether and treated with 5.0 mL of butyllithium in hexanes (2.5 M, 12.5 mmol) at −78 C. After stirring at room temperature for 3 h, 95 micro liter of N-methyl-imidazole were added by syringe and stirred for 15 minutes. THF (ca. 30 ml) was added at 0° C. to give a clear solution just prior to addition to the chlorosilane described below. 4-(4-tert-Butyl-phenyl)-2-isopropyl-1H-indene (3.5 g, 12.1 mmol) was dissolved in ether (50 ml) and treated with 5.2 ml of butyllithium in hexanes (2.5 M, 13.0 mmol) at −40 C. After stirred at room temperature for 3 h, 15.6 mmol of dichlorodimethylsilane were added by syringe at −78 C. The mixture was stirred for 16 h at room temperature, filtered, and solvents removed in vacuo from the filtrate leaving an amorphous solid product. The product was dissolved in THF, cooled to −78° C., and treated with an ether/THF solution of the lithio salt of 4-(2,5-dimethylphenyl)-6-methyl-1,2,3,5-tetrahydro-s-indacene prepared as described above. The mixture was warmed to room temperature and stirred overnight before quenching the reaction with 10 ml of a saturated aqueous solution of NH$_4$Cl. The organic phase was separated, washed with 40 ml of brine solution, dried (MgSO$_4$), and evaporated to an oil. Chromatography on silica (10% CH$_2$Cl$_2$ in heptane) gave 7.0 g of product as a white solid (84% yield).

$^1$H NMR (CDCl$_3$): 7.1-8.0 (m, 13H), 6.5 (s, 1H), 4.0-4.4 (m, 2H), 2.8-3.4 (m, 6H), 2.7 (s, 3H), 1.8 (s, 9H), 1.5 (m, 3H), 1.2 (m, 3H), 0.0-0.4 (m, 6H).

EIMS: m/z (%) 620 (M$^+$, 4), 331 (100), 291 (19), 271 (9), 243 (7), 215 (5), 191 (2), 165 (2). 6 Preparation of dimethylsilanediyl-(6-methyl-4-(2,5-dimethylphenyl)-1,2,3,5-tetrahydro-s-indacen-7-yl)-(2-isopropyl-4-(4'-tert-butylphenyl)-1-indenyl)-zirconium dichloride (6) Dimethyl-(4-(2,5-dimethylphenyl)-6-methyl-1,2,3,5-tetrahydro-s-indacenyl) (2-i-propyl-4-(4-t-butylphenyl)-1-indenyl)-silane (5.5 g, 8.9 mmol) was dissolved in 50 ml of ether, cooled to −10° C., and treated with 7.4 ml of butyllithium in hexanes (2.5 M, 18.2 mmol). After stirring at room temperature for 4 h, solvents were removed under reduced pressure and zirconium(IV) chloride (2.07 g, 8.9 mmol) was added as a dry powder. The mixture was stirred in 40 ml of pentane for 10 minutes and then 40 ml of ether were added at 0° C. The flask and contents were warmed to room temperature and the reaction mixture stirred overnight. The resulting yellow-orange precipitate was collected on a closed fritted funnel, washed with ether, pentane, and dried in vacuo (4.05 g). The product was recrystallized in toluene to give 1.5 g of metallocene (22% yield, >90% racemic form).

$^1$H NMR (CDCl$_3$): 7.5-7.7 (m, 2H), 7.4-7.5 (m, 2H), 7.3-7.4 (m, 2H), 7.0-7.2 (m, 3H), 6.35 (s, 1H), 3.3-3.5 (m, 1H), 2.8-3.0 (m, 3H), 2.4 (m, 1H), 2.3 (s, 3H), 2.2 (s, 3H), 2.0 (m, 2H), 1.9 (s, 3H), 1.2-1.4 (s, 9H; s, 3H; s, 3H, d, 3H), 1.1 (d, 3H).

7. Dimethylsilanediyl-(2-Me-5-iPr-3-Ph-cyclopento[2,3-b]thiophen-6-yl)(6-Me-8-Ph-1,2,3,5-tetrahydro-s-indacenyl)-zirconium dichloride (7)

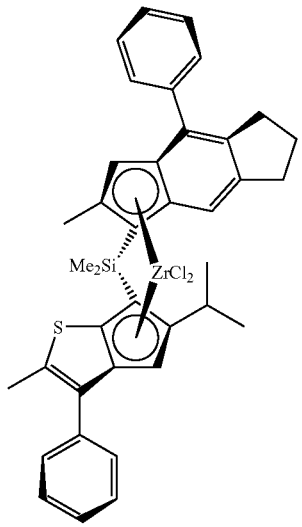

(7)

7a Preparation of (6-Me-8-Ph-1,2,3,5-tetrahydro-s-indacenyl)(2-Me-5-iPr-3-Ph-6-hydrocyclopenta[2,3-b]thiophen-6-yl)SiMe$_2$ (7a)

2-Me-5-iPr-3-Ph-4-hydrocyclopenta[2,1-b]thiophene (7.0 g, 0.0276 mol, prepared as described in WO 03/045964) was dissolved in 75 ml of ether and treated with 11.6 ml of butyllithium in hexanes (2.5 M, 0.029 mol) at 0° C. After stirring at room temperature for 4 h, the mixture was cooled to −78° C., and 5.0 ml (0.414 mol) of dichlorodimethylsilane were syringed into the flask. The reaction mixture was warmed to room temperature, stirred for 16 h, filtered, and volitles removed from the filtrate in vacuo. The residue was redissolved in 60 ml of THF, cooled to −78° C., and treated with a THF/ether solution of the lithium salt of 6-Me-8-Ph-1,2,3,5-tetrahydro-s-indacene (60 ml, 0.0295 mol) prepared as described below. After stirring for 18 h at room temperature, 20 ml of a saturated aqueous solution of NH$_4$Cl were added. The organic fraction was separated, washed with brine solution, and dried (MgSO$_4$). A dark brown oil (15.7 g) was recovered after evaporating the solvents on a rotoevaporator. The crude product was chromatographed on silica (10% CH$_2$Cl$_2$ in hexanes) to give the product (7a) as a white solid (11.0 g, 71%).

$^1$H-NMR δ (CDCl$_3$): 7.3-7.8 (m, 11H), 6.7-6.9 (m, 2H), 3.9-4.2 (4 singlets, 2H total), 2.9-3.3 (m, 4H), 2.7-2.8 (m, 3H), 2.2-2.5 (m, 4H), 1.2-1.6 (m, 8H), 0.0-0.5 (multiplet & 3 singlets, 6H total).

Preparation of 6-Me-8-Ph-1,2,3,5-tetrahydro-s-indacenyl lithium used above 7.1 g (0.295 mol) of 6-Methyl-8-phenyl-1,2,3,5-tetrahydro-s-indacene were dissolved in 60 ml of ether and treated with 11.8 ml of butyllithium in hexanes (2.5 M, 0.295 mol) at 0° C. After stirring for 4 h at room temperature, 230 μl of N-Me-imidazole were added by syringe and stirred for 15 minutes. The mixture was cooled to 0° C. and THF was added until all solids dissolved (ca. 15 ml). The solution was used immediately in the above reaction.

7 Preparation of dimethylsilanediyl-(2-Me-5-iPr-3-Ph-cyclopento[2,3-b]thiophen-6-yl)(6-Me-8-Ph-1,2,3,5-tetrahydro-s-indacenyl)-zirconium dichloride (7)

6.58 g (0.0118 mol) of (6-Me-8-Ph-1,2,3,5-tetrahydro-s-indacenyl)(2-Me-5-iPr-3-Ph-6-hydrocyclopenta[2,3-b]thiophen-6-yl)SiMe$_2$ were dissolved in 60 ml of ether, treated with 9.9 ml of butyllithium in hexanes (2.5 M, 0.0248 mol) at 0° C., and stirred at room temperature for 4 h. Solvents were removed from the orange slurry in vacuo, ZrCl$_4$ (2.7 g, 0.012 mol) was added, and the mixture was stirred in 40 ml of pentane for 10 minutes. Ether (40 ml) was added and stirring continued for 48 h. The resulting yellow solids were collected on a closed fritted funnel, washed with ether, and dried in vacuo (3.3 g). NMR analysis showed this fraction to contain predominately the pseudo-racemic form. The filtrate was evaporated to yellow-orange solids (5.4 g). NMR analysis showed this fraction to be a mixture of the pseudo racemic & meso forms plus impurities. The yellow insolubles were refluxed in DME with 1.0 g of LiCl for 5 h. After cooling, the insolubles were collected on a closed fritted funnel and extracted with dichloromethane (100 ml). In-situ evaporation of the extract gave 0.5 g of pure pseudo-racemic {Me$_2$Si(2-Me-5-iPr-3-Ph-cyclopento[2,3-b]thiophen-6-yl)(6-Me-8-Ph-1,2,3,5-tetrahydro-s-indacenyl)}ZrCl$_2$.

$^1$H-NMR δ (CDCl$_3$): (pseudo-racemic form) 7.2-7.6 (m, 11H), 6.7 (s, 1H), 6.5 (s, 1H), 3.15-3.3 (m, 1H), 2.9-3.05 (m, 3H), 2.7-2.9 (m, 1H), 2.55 (s, 3H), 2.35 (s, 3H), 2.0 (m, 2H), 1.3 (s, 3H), 1.1 (s, 3H & d, 3H), 0.95 (d, 3H); (pseudo-meso form) 7.2-7.6 (m, 11H), 6.6 (s, 1H), 6.45 (s, 1H), 2.9-3.1 (m, 4H), 2.6-2.8 (m, 1H), 2.4 (s, 3H), 2.3 (s, 3H), 1.8-2.2 (m, 2H), 1.4 (d, 3H), 1.35 (s, 3H), 1.2 (s, 3H & d, 3H).

The following metallocenes were used in the polymerization experiments:

| Metallocene (MC) No. | Structure |
| --- | --- |
| 1 | Me$_2$Si(6-Me-4-(p-$^t$Bu-Ph)-1,2,3,5-tetrahydro-s-indacen-7-yl)(2-$^i$Pr-4-(p-$^t$Bu-Ph)-1-Ind)ZrCl$_2$ (from example 1) |
| 2 | Me$_2$Si(6-Me-4-Ph-1,2,3,5-tetrahydro-s-indacen-7-yl)(2-$^i$Pr-4-(p-$^t$Bu-Ph)-1-Ind)ZrCl$_2$ (from example 2) |

-continued

| Metallocene (MC) No. | Structure |
|---|---|
| 3 | Me$_2$Si(6-Me-4-Ph-1,2,3,5-tetrahydro-s-indacen-7-yl)(2-$^i$Pr-4-Ph-1-Ind)ZrCl$_2$ (from example 3) |
| 4 | Me$_2$Si(2-Me-4-(p-$^t$Bu-Ph)-tetrahydrocyclopenta[b]naphthalenyl)(2-$^i$Pr-4-Ph-1-Ind)ZrCl$_2$ (from example 4) |
| 5 | Me$_2$Si(6-Me-4,8-Ph$_2$-1,2,3,5-tetrahydro-s-indacen-7-yl)(2-$^i$Pr-4-Ph-1-Ind)ZrCl$_2$ (from example 5) |
| 6 | Me$_2$Si(6-Me-4-(2,5-Me$_2$Ph)-1,2,3,5-tetrahydro-s-indacen-7-yl)(2-$^i$Pr-4-(p-$^t$Bu-Ph)-1-Ind)ZrCl$_2$ (from example 6) |
| 7 | Me$_2$Si(2-Me-5-iPr-3-Ph-cyclopento[2,3-b]thiophen-6-yl)(6-Me-8-Ph-1,2,3,5-tetrahydro-s--indacenyl)ZrCl$_2$ (from example 7) |
| C1 | Me$_2$Si(2-Me-4-(p-$^t$Bu-Ph)-1-Ind)(2-$^i$Pr-4-(p-$^t$Bu-Ph)-1-Ind)ZrCl$_2$ |
| C2 | Me$_2$Si(2,6-Me$_2$-4-(p-$^t$Bu-Ph)-1-Ind)(2-$^i$Pr-4-(p-$^t$Bu-Ph)-1-Ind)ZrCl$_2$ |
| C3 | Me$_2$Si(2,7-Me$_2$-4-(p-$^t$Bu-Ph)-1-Ind)(2-$^i$Pr-4-(p-$^t$Bu-Ph)-1-Ind)ZrCl$_2$ |

Homopolymerizations and polymer analysis

| Example | MC No. | Amount | Propylene | H$_2$ | Activity | T$_m$ | I.V. | M$_w$ | Q |
|---|---|---|---|---|---|---|---|---|---|
| P 1 | 1 | 603 mg | 3.5 kg | no | 1.0 | 159.0 | 3.72 | 548 | 2.7 |
| P 2 | 1 | 405 mg | 3.5 kg | yes | 3.9 | 157.6 | 1.86 | 251 | 2.7 |
| P 3 | 2 | 599 mg | 3.5 kg | no | 1.0 | 157.8 | 4.11 | 591 | 3.4 |
| P 4 | 2 | 397 mg | 3.5 kg | yes | 3.4 | 155.7 | 2.22 | 298 | 3.5 |
| P 5 | 3 | 50 mg | 3.5 kg | no | 1.5 | 155.0 | 3.6 | 559 | 2.4 |
| P 6 | 3 | 50 mg | 3.5 kg | yes | 2.4 | 155.7 | 1.9 | 229 | 1.9 |
| P 7 | 4 | 608 mg | 3.5 kg | No | 1.2 | 155.7 | 4.3 | 627 | 3.1 |
| P 8 | 4 | 243 mg | 3.5 kg | Yes | 5.8 | 156.5 | 2.2 | 271 | 3.4 |
| P 7 | 5 | 50 mg | 3.5 kg | no | 1.9 | 160.3 | 2.77 | 355 | 2.1 |
| P 8 | 5 | 50 mg | 3.5 kg | yes | 3.9 | 159.1 | 2.06 | 253 | 1.9 |
| P 9 | 6 | 50 mg | 3.5 kg | no | 2.0 | 157.4 | 4.57 | 795 | 2.8 |
| P 10 | 6 | 50 mg | 3.5 kg | yes | 3.9 | 159.3 | 1.74 | 219 | 2.2 |
| P 11 | 7 | 598 mg | 3.5 kg | no | 1.3 | 154.0 | 3.49 | 474 | 3.0 |
| cP 1 | C1 | 570 mg | 3.5 kg | no | 0.6 | 152.5 | 2.53 | 356 | 2.3 |
| cP 2 | C1 | 650 mg | 3.5 kg | yes | 2.7 | 154.3 | 1.94 | 240 | 2.2 |
| cP 3 | C2 | 730 mg | 3.5 kg | no | 1.2 | 155.4 | 3.00 | 458 | 2.4 |
| cP 4 | C2 | 650 mg | 3.5 kg | yes | 2.9 | 153.3 | 1.87 | 235 | 2.5 |
| cP 5 | C3 | 590 mg | 3.5 kg | no | 1.4 | 155.7 | 2.67 | 401 | 2.5 |
| cP 6 | C3 | 286 mg | 3.5 kg | yes | 7.1 | 158.2 | 1.80 | 214 | 2.1 |

Units and abbreviations: Activity: kg/(g*h); melting point (T$_m$); ° C.; viscosity number (I.V.): dl/g; weight average molar mass (M$_w$): 10$^3$ g/mol; polydispersity: Q = M$_w$/M$_n$ Copolymerizations and polymer analysis

| Example | MC No. | Amount | Activity | I.V. | M$_w$ | Q | T$_m$ | C2 content |
|---|---|---|---|---|---|---|---|---|
| P 12 | 1 | 199 mg | 7.4 | 4.80 | 909 | 3.1 | 123.3 | 3.8 |
| P 13 | 2 | 205 mg | 3.1 | 4.91 | 728 | 3.9 | 123.5 | 4.7 |
| P 14 | 3 | | | | | | | |
| P 15 | 4 | 210 mg | 3.5 | 5.82 | 883 | 3.3 | 128.3 | 4.0 |
| P 16 | 5 | 40 mg | 4.2 | 4.3 | 594 | 2.31 | 108.1 | 6.2 |
| P 17 | 6 | 40 mg | 4.2 | 4.95 | 994 | 3.7 | 119.7 | 4.7 |
| P 18 | 7 | 210 mg | 11.9 | 3.92 | 574 | 2.91 | 118.0 | 5.0 |
| cP 7 | C1 | 209 mg | 3.4 | 2.86 | 433 | 2.3 | 125.8 | 3.2 |
| cP 8 | C2 | 207 mg | 5.4 | 3.71 | 608 | 2.7 | 122.8 | 3.4 |
| cP 9 | C3 | 196 mg | 7.0 | 3.25 | 452 | 2.5 | 118.3 | 4.6 |

Units and abbreviations: Activity: kg/(g*h); melting point (T$_m$); ° C.; viscosity number (I.V.): dl/g; weight average molar mass (M$_w$): 10$^3$ g/mol; polydispersity: Q = M$_w$/M$_n$; C2 content: % by weight

We claim:

1. An organometallic transition metal compound of the formula (I):

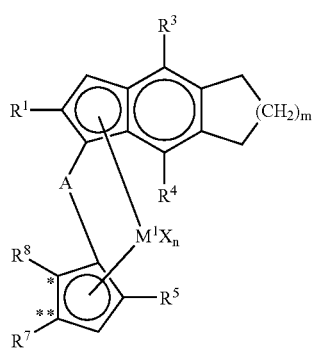

(I)

where
- $M^1$ is an element of group 3, 4, 5 or 6 of the Periodic Table of the Elements or the lanthanides;
- the radicals X are identical or different and are each an organic or inorganic radical, with two radicals X also being able to be joined to one another;
- m is 1 or 2;
- n is a natural number from 1 to 4;
- $R^1$ is hydrogen or an organic radical having from 1 to 40 carbon atoms;
- $R^3$ is a substituted or unsubstituted $C_6$-$C_{40}$ aryl radical;
- $R^4$ is hydrogen, halogen or an organic radical having from 1 to 40 carbon atoms;
- $R^5$ is an organic radical which has from 3 to 20 carbon atoms and is branched in the α position;
- $R^7$, $R^8$ are identical or different and are each hydrogen or an organic radical having from 1 to 40 carbon atoms or $R^7$ and $R^8$ together with the atoms connecting them form a monocyclic or polycyclic, substituted or unsubstituted ring system which has from 1 to 40 carbon atoms and optionally contains heteroatoms selected from the group consisting of the elements Si, Ge, N, P, O, S, Se and Te; and
- A is a bridge consisting of a divalent atom or a divalent group.

2. The compound of claim 1 wherein $R^1$ and $R^5$ are different.

3. The compound of claim 1 wherein $M^1$ is a Group 4 transition metal and n=2.

4. The compound of claim 1 wherein $R^7$, $R^8$ together form

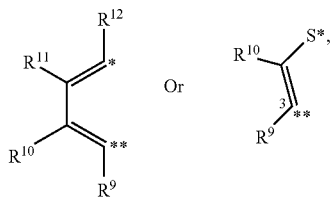

where
$R^9$, $R^{10}$, $R^{11}$ and $R^{12}$ are identical or different and are each hydrogen, halogen or an organic radical having from 1 to 40 carbon atoms or two adjacent radicals $R^9$, $R^{10}$ and/or $R^{11}$ together with the atoms connecting them form a monocyclic or polycyclic, substituted or unsubstituted ring system which has from 1 to 40 carbon atoms and optionally contains heteroatoms selected from the group consisting of the elements Si, Ge, N, P, O, S, Se and Te; and
A is a substituted silylene group or a substituted or unsubstituted ethylene group.

5. A biscyclopentadienyl ligand system of the formula (II):

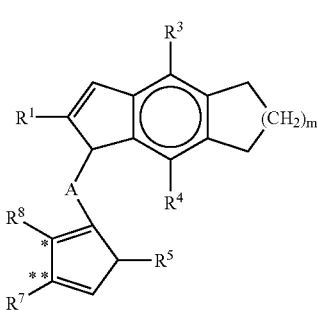

(II)

or its double bond isomers,
wherein
- m is 1 or 2;
- $R^1$ is hydrogen or an organic radical having from 1 to 40 carbon atoms;
- $R^3$ is a substituted or unsubstituted $C_6$-$C_{40}$ aryl radical;
- $R^4$ is hydrogen, halogen or an organic radical having from 1 to 40 carbon atoms;
- $R^5$ is an organic radical which has from 3 to 20 carbon atoms and is branched in the α position;
- $R^7$, $R^8$ are identical or different and are each hydrogen or an organic radical having from 1 to 40 carbon atoms or $R^7$ and $R^8$ together with the atoms connecting them form a monocyclic or polycyclic, substituted or unsubstituted ring system which has from 1 to 40 carbon atoms and optionally contains heteroatoms selected from the group consisting of the elements Si, Ge, N, P, O, S, Se and Te; and
- A is a bridge consisting of a divalent atom or a divalent group.

6. A catalyst system for the polymerization of olefins, which comprises:
(a) at least one organometallic transition metal compound of claim 1; and
(b) at least one cocatalyst which converts the at least one organometallic transition metal compound into a species which is polymerization-active toward at least one olefin.

7. The catalyst system of claim 6 further comprising a support.

8. A process which comprises polymerizing or copolymerizing at least one olefin in the presence of the catalyst system of claim 6.

9. A process for preparing an organometallic transition metal compound, which comprises reacting the biscyclopentadienyl ligand system of claim 5 or a bisanion prepared therefrom with a transition metal compound.

* * * * *